United States Patent
Joshi et al.

(10) Patent No.: US 9,265,958 B2
(45) Date of Patent: Feb. 23, 2016

(54) IMPLANTABLE MEDICAL DEVICE ANTENNA

(75) Inventors: Himanshu Joshi, Houston, TX (US); Eric Y. Chow, Houston, TX (US); Clint Warren, Dickinson, TX (US)

(73) Assignee: CYBERONICS, INC., Houston, TX (US)

( * ) Notice: Subject to any disclaimer, the term of this patent is extended or adjusted under 35 U.S.C. 154(b) by 991 days.

(21) Appl. No.: 13/328,241

(22) Filed: Dec. 16, 2011

(65) Prior Publication Data

US 2012/0276856 A1  Nov. 1, 2012

Related U.S. Application Data

(63) Continuation-in-part of application No. 13/098,279, filed on Apr. 29, 2011, now abandoned.

(51) Int. Cl.

| | |
|---|---|
| A61N 1/37 | (2006.01) |
| A61B 5/00 | (2006.01) |
| A61N 1/372 | (2006.01) |
| H01Q 1/38 | (2006.01) |
| H01Q 21/08 | (2006.01) |
| H01Q 21/20 | (2006.01) |
| H01Q 1/27 | (2006.01) |
| H01Q 1/52 | (2006.01) |
| H01Q 7/00 | (2006.01) |
| H01Q 9/04 | (2006.01) |
| H01Q 13/10 | (2006.01) |
| H01Q 21/30 | (2006.01) |
| A61N 1/375 | (2006.01) |
| A61N 1/378 | (2006.01) |

(52) U.S. Cl.
CPC ............ *A61N 1/37229* (2013.01); *H01Q 1/273* (2013.01); *H01Q 1/38* (2013.01); *H01Q 1/521* (2013.01); *H01Q 7/00* (2013.01); *H01Q 9/045* (2013.01); *H01Q 13/106* (2013.01); *H01Q 21/08* (2013.01); *H01Q 21/205* (2013.01); *H01Q 21/30* (2013.01); *A61N 1/375* (2013.01); *A61N 1/3787* (2013.01); *Y10T 29/49018* (2015.01)

(58) Field of Classification Search
CPC ...................... A61N 1/37229; A61B 2018/183
See application file for complete search history.

(56) References Cited

U.S. PATENT DOCUMENTS

| | | |
|---|---|---|
| 4,030,480 A | 6/1977 | Meyer |
| 4,075,632 A | 2/1978 | Baldwin et al. |
| 4,127,110 A | 11/1978 | Bullara |
| 4,305,397 A | 12/1981 | Weisbrod et al. |
| 4,414,979 A | 11/1983 | Hirshorn et al. |
| 4,441,498 A | 4/1984 | Nordling |
| RE32,361 E | 2/1987 | Duggan |
| 4,800,899 A | 1/1989 | Elliott |

(Continued)

OTHER PUBLICATIONS

International Application No. PCT/US2012/032007, International Search Report and Written Opinion of the International Searching Authority dated Sep. 13, 2013, 13 pages.

(Continued)

*Primary Examiner* — Christopher D Koharski
*Assistant Examiner* — Natasha Patel

(57) ABSTRACT

An implantable medical device includes a case having a conductive housing defining an opening. A dielectric material is coupled to the conductive housing to hermetically seal the opening. An antenna is within the case under the dielectric material. A header block is coupled to the case over the dielectric material.

22 Claims, 16 Drawing Sheets

(56) References Cited

U.S. PATENT DOCUMENTS

| | | |
|---|---|---|
| 4,823,812 A | 4/1989 | Eshel et al. |
| 5,035,231 A | 7/1991 | Kubokawa et al. |
| 5,050,605 A | 9/1991 | Eydelman et al. |
| 5,058,581 A | 10/1991 | Silvian |
| 5,109,853 A | 5/1992 | Taicher et al. |
| 5,117,825 A | 6/1992 | Grevious |
| 5,168,871 A | 12/1992 | Grevious |
| 5,246,000 A | 9/1993 | Ellis et al. |
| 5,313,953 A | 5/1994 | Yomtov et al. |
| 5,314,453 A | 5/1994 | Jeutter |
| 5,330,518 A | 7/1994 | Neilson et al. |
| 5,336,245 A | 8/1994 | Adams et al. |
| 5,350,411 A | 9/1994 | Ryan et al. |
| 5,373,852 A | 12/1994 | Harrison et al. |
| 5,375,596 A | 12/1994 | Twiss et al. |
| 5,383,912 A | 1/1995 | Cox et al. |
| 5,402,788 A | 4/1995 | Fujio et al. |
| 5,456,698 A | 10/1995 | Byland et al. |
| 5,494,030 A | 2/1996 | Swartz et al. |
| 5,558,618 A | 9/1996 | Maniglia |
| 5,562,714 A | 10/1996 | Grevious |
| 5,629,678 A | 5/1997 | Gargano et al. |
| 5,630,835 A | 5/1997 | Brownlee |
| 5,697,958 A | 12/1997 | Paul et al. |
| 5,720,770 A | 2/1998 | Nappholz et al. |
| 5,735,887 A | 4/1998 | Barreras, Sr. et al. |
| 5,766,232 A | 6/1998 | Grevious et al. |
| 5,782,891 A | 7/1998 | Hassler et al. |
| 5,788,692 A | 8/1998 | Campbell et al. |
| 5,800,494 A | 9/1998 | Campbell et al. |
| 5,840,148 A | 11/1998 | Campbell et al. |
| 5,861,019 A | 1/1999 | Sun et al. |
| 5,873,840 A | 2/1999 | Neff |
| 5,902,251 A | 5/1999 | vanHooydonk |
| 5,928,145 A | 7/1999 | Ocali et al. |
| 5,951,594 A | 9/1999 | Kerver |
| 5,963,132 A | 10/1999 | Yoakum |
| 5,967,986 A | 10/1999 | Cimochowski et al. |
| 6,009,350 A | 12/1999 | Renken |
| 6,009,878 A | 1/2000 | Weijand et al. |
| 6,041,256 A | 3/2000 | Michel |
| 6,073,050 A | 6/2000 | Griffith |
| 6,115,634 A | 9/2000 | Donders et al. |
| 6,161,049 A | 12/2000 | Rudie et al. |
| 6,167,312 A | 12/2000 | Goedeke |
| 6,169,925 B1 | 1/2001 | Villaseca et al. |
| 6,175,768 B1 | 1/2001 | Arndt et al. |
| 6,176,856 B1 | 1/2001 | Jandak et al. |
| 6,190,382 B1 | 2/2001 | Ormsby et al. |
| 6,192,279 B1 | 2/2001 | Barreras, Sr. et al. |
| 6,201,993 B1 | 3/2001 | Kruse et al. |
| 6,240,317 B1 | 5/2001 | Villaseca et al. |
| 6,261,247 B1 | 7/2001 | Ishikawa et al. |
| 6,275,737 B1 | 8/2001 | Mann |
| 6,277,113 B1 | 8/2001 | Berube |
| 6,308,101 B1 | 10/2001 | Faltys et al. |
| 6,308,102 B1 | 10/2001 | Sieracki et al. |
| 6,379,300 B1 | 4/2002 | Haubrich |
| 6,393,327 B1 | 5/2002 | Scribner |
| 6,398,710 B1 | 6/2002 | Ishikawa et al. |
| 6,456,256 B1 | 9/2002 | Amundson et al. |
| 6,463,329 B1 | 10/2002 | Goedeke |
| 6,477,425 B1 | 11/2002 | Nowick et al. |
| 6,485,462 B1 | 11/2002 | Kriesel |
| 6,505,072 B1 | 1/2003 | Linder et al. |
| 6,516,227 B1 | 2/2003 | Meadows et al. |
| 6,556,169 B1 | 4/2003 | Fukuura et al. |
| 6,561,975 B1 | 5/2003 | Pool et al. |
| 6,574,510 B2 | 6/2003 | Von Arx et al. |
| 6,610,054 B1 | 8/2003 | Edwards et al. |
| 6,614,406 B2 | 9/2003 | Amundson et al. |
| 6,631,290 B1 | 10/2003 | Guck et al. |
| 6,675,810 B2 | 1/2004 | Krag |
| 6,682,480 B1 | 1/2004 | Habib et al. |
| 6,708,065 B2 | 3/2004 | Von Arx et al. |
| 6,805,667 B2 | 10/2004 | Christopherson et al. |
| 6,894,616 B1 | 5/2005 | Forster |
| 6,922,591 B2 | 7/2005 | Single |
| 6,924,773 B1 | 8/2005 | Paratte |
| 7,016,733 B2 | 3/2006 | Dublin et al. |
| 7,042,357 B2 | 5/2006 | Girvin et al. |
| 7,043,307 B1 | 5/2006 | Zelickson et al. |
| 7,064,725 B2 | 6/2006 | Shtrikman et al. |
| 7,092,763 B1 | 8/2006 | Griffith et al. |
| 7,146,861 B1 | 12/2006 | Cook et al. |
| 7,149,578 B2 | 12/2006 | Edvardsson |
| 7,174,212 B1 | 2/2007 | Klehn et al. |
| 7,191,013 B1 | 3/2007 | Miranda et al. |
| 7,203,549 B2 | 4/2007 | Schommer et al. |
| 7,209,792 B1 | 4/2007 | Parramon et al. |
| 7,212,866 B1 | 5/2007 | Griffith |
| 7,235,096 B1 | 6/2007 | Van Tassel et al. |
| 7,281,314 B2 | 10/2007 | Hess et al. |
| 7,286,877 B2 | 10/2007 | Daum |
| 7,317,946 B2 | 1/2008 | Twetan et al. |
| 7,399,280 B2 | 7/2008 | Liu et al. |
| 7,429,255 B2 | 9/2008 | Thompson |
| 7,432,723 B2 | 10/2008 | Ellis et al. |
| 7,483,732 B2 | 1/2009 | Zhong et al. |
| 7,483,752 B2 | 1/2009 | Von Arx et al. |
| 7,554,493 B1 | 6/2009 | Rahman |
| 7,561,921 B2 | 7/2009 | Phillips et al. |
| 7,577,476 B2 | 8/2009 | Hochman et al. |
| 7,695,435 B2 | 4/2010 | Benson et al. |
| 7,729,766 B2 | 6/2010 | Toy et al. |
| 7,860,476 B1 | 12/2010 | Karr et al. |
| 7,904,167 B2 | 3/2011 | Klosterman et al. |
| 7,907,091 B2 | 3/2011 | Zhang |
| 7,983,760 B2 | 7/2011 | Ginggen et al. |
| 8,253,640 B2 | 8/2012 | Kitayoshi et al. |
| 8,332,037 B2 | 12/2012 | Imran |
| 8,442,643 B2 | 5/2013 | Toy et al. |
| 8,565,891 B2 | 10/2013 | Mumbru et al. |
| 8,599,086 B2 | 12/2013 | Wong et al. |
| 8,725,263 B2 | 5/2014 | Yamamoto et al. |
| 2002/0095195 A1* | 7/2002 | Mass et al. ............ 607/60 |
| 2005/0113886 A1 | 5/2005 | Fischell et al. |
| 2005/0222633 A1* | 10/2005 | Edvardsson ............ 607/36 |
| 2006/0028784 A1 | 2/2006 | Brendel |
| 2006/0247712 A1* | 11/2006 | Fuller et al. ............ 607/32 |
| 2007/0043399 A1 | 2/2007 | Stevenson |
| 2007/0123949 A1* | 5/2007 | Dabney et al. ............ 607/37 |
| 2007/0273606 A1* | 11/2007 | Mak et al. ............ 343/876 |
| 2008/0033500 A1 | 2/2008 | Strother et al. |
| 2008/0091242 A1 | 4/2008 | Kamath et al. |
| 2008/0198082 A1 | 8/2008 | Castany et al. |
| 2008/0316112 A1 | 12/2008 | Zhang |
| 2009/0228075 A1 | 9/2009 | Dion |
| 2009/0248112 A1 | 10/2009 | Mumbru et al. |
| 2010/0060431 A1 | 3/2010 | Stevenson et al. |
| 2010/0082080 A1 | 4/2010 | Mateychuk |
| 2010/0109966 A1 | 5/2010 | Mateychuk et al. |
| 2010/0114205 A1 | 5/2010 | Donofrio et al. |
| 2010/0114225 A1* | 5/2010 | Imran et al. ............ 607/9 |
| 2010/0149042 A1 | 6/2010 | Utsi |
| 2010/0161002 A1* | 6/2010 | Aghassian et al. ............ 607/60 |
| 2010/0168818 A1 | 7/2010 | Barror et al. |
| 2010/0194541 A1 | 8/2010 | Stevenson et al. |
| 2010/0321163 A1 | 12/2010 | Stevenson |
| 2011/0004076 A1 | 1/2011 | Janna et al. |
| 2012/0071942 A1 | 3/2012 | Kamath et al. |
| 2012/0326886 A1 | 12/2012 | Herman et al. |
| 2013/0289666 A1 | 10/2013 | Johnson et al. |

OTHER PUBLICATIONS

International Application No. PCT/US2012/032007, International Search Report and Written Opinion of the International Searching Authority dated Sep. 13, 2013, 13 pages., 13 pages.

* cited by examiner

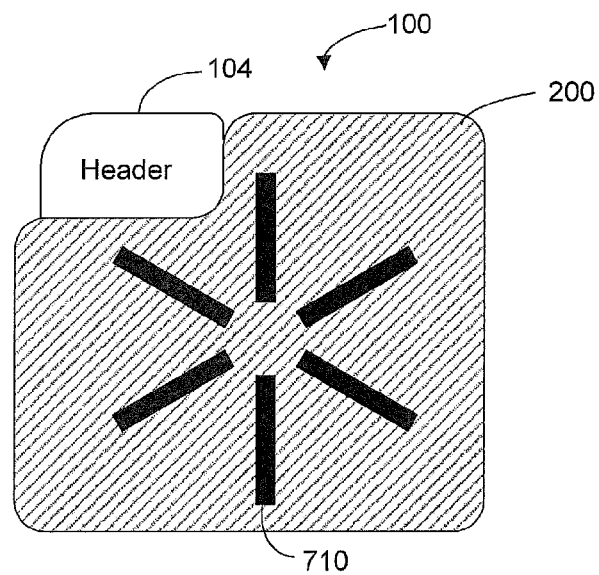
FIG. 7A
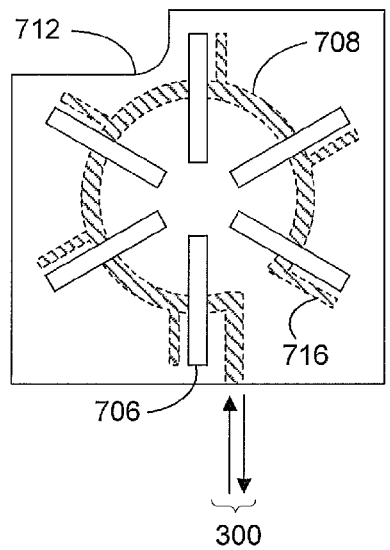   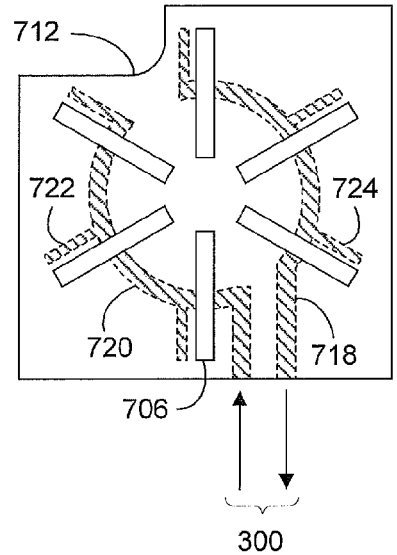
FIG. 7B     FIG. 7C

IMPLANTABLE MEDICAL DEVICE ANTENNA

CLAIM OF PRIORITY

This application is a continuation-in-part of and claims priority to U.S. patent application Ser. No. 13/098,279 filed Apr. 29, 2011, which is incorporated herein by reference in its entirety.

FIELD OF THE DISCLOSURE

The present disclosure is generally related to implantable medical devices with internal antennas.

SUMMARY

A particular embodiment of the disclosure relates to an implantable medical device which includes a case having a conductive housing defining an opening. A dielectric material is coupled to the conductive housing to hermetically seal the opening. An antenna is within the case under the dielectric material. A header block is coupled to the case over the dielectric material.

Another particular embodiment of the disclosure relates to a method that includes positioning an antenna in a portion of a case of an implantable medical device. The case includes a conductive housing that defines an opening and a dielectric material coupled to the conductive housing to hermetically seal the opening. The antenna is positioned under the dielectric material. The method also includes hermetically sealing the case and coupling a header block to the case over the dielectric material.

Another particular embodiment of the disclosure relates to a method that includes receiving a signal at a first antenna that is hermetically sealed within an implantable medical device. The implantable medical device includes a case including a conductive housing defining an opening, a dielectric material coupled to the conductive housing to hermetically seal the opening, and a header block over the dielectric material. The first antenna is positioned within the case under the dielectric material and under the header block. The method also includes performing an action at the implantable medical device in response to the signal.

BRIEF DESCRIPTION OF THE DRAWINGS

The disclosure will become more fully understood from the following detailed description, taken in conjunction with the accompanying drawings.

FIGS. 7A-7C illustrate an implantable medical device having multiple cutouts according to an exemplary embodiment.

DETAILED DESCRIPTION

Figure 1:
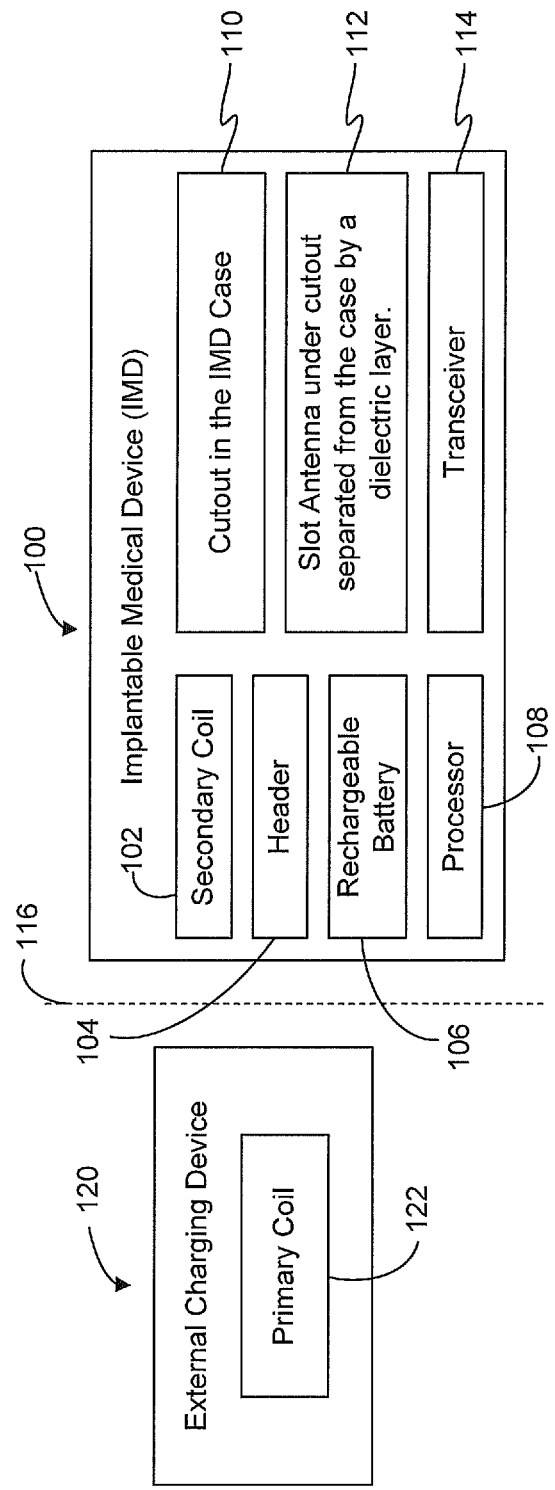
FIG. 1 is a block diagram of the implantable medical device and an external charging device according to an exemplary embodiment.

Referring to FIG. 1, a block diagram of an implantable medical device (IMD) 100 and an external charging device 120 are shown according to an exemplary embodiment. The MD 100 may include a secondary coil 102, a header 104, a rechargeable battery 106, a processor 108, a dielectric filled cutout 110 in the IMD case, a slot antenna 112, and a transceiver 114 according to one exemplary embodiment. The external charging device 120 may include a primary coil 122 according to an exemplary embodiment.

The header 104 may be configured to couple one or more wire leads to the IMD 100. The wire leads may include electrodes for sensing or delivering therapy, such as delivering electrical stimulation to neural tissue. The primary coil 122 of the external charging device 120 may be configured to inductively couple to the secondary coil 102 of the IMD 100 across a tissue barrier 116 of a patient, such as the patient's skin. The primary coil 122 may be configured to induce a current in the secondary coil 102. The secondary coil 102 may be coupled to the rechargeable battery 106 and operative to recharge the rechargeable battery 106 using the induced current. The processor 108 may be configured to monitor the recharging of the rechargeable battery 106 and to restrict further recharging once the rechargeable battery 106 is sufficiently charged.

Figure 2:
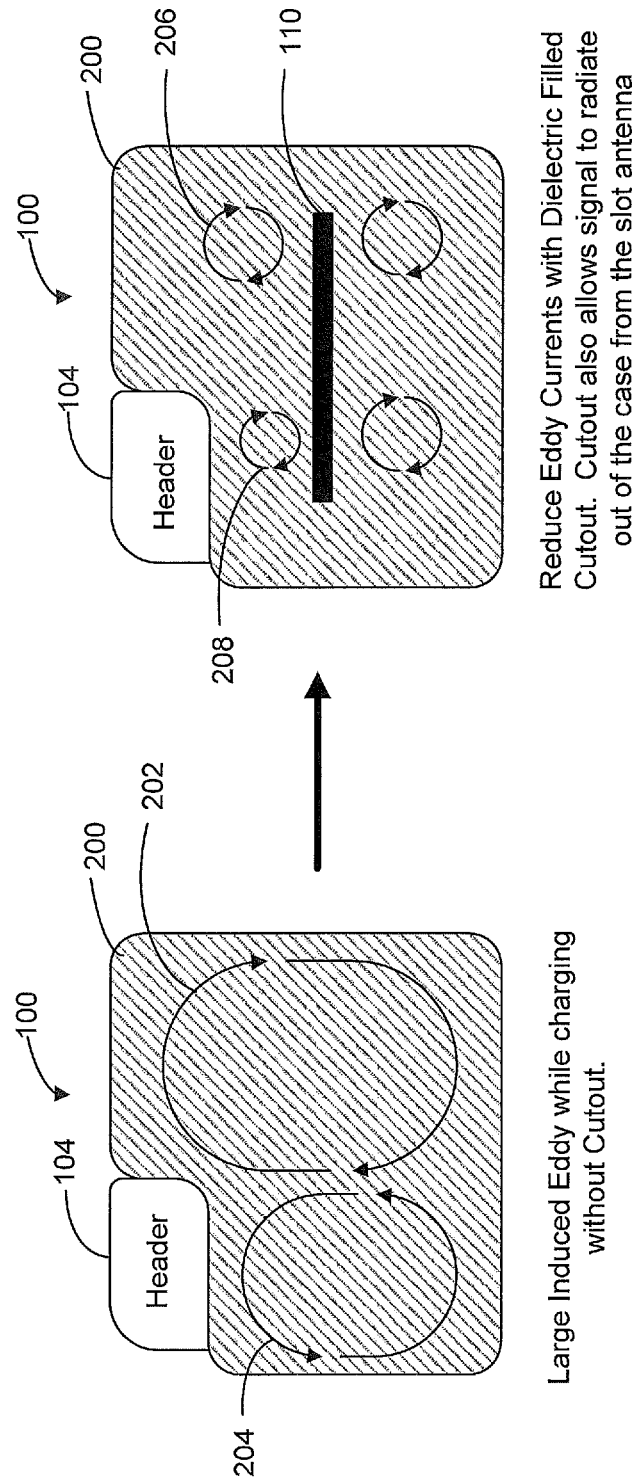
FIGS. 2A-2B illustrate an implantable medical device with large eddy currents and an implantable medical device with smaller eddy currents according to an exemplary embodiment.

The cutout 110 may be one or more cutouts in a conductive case of the IMD 100, as described in FIGS. 2A-2B. The cutout 110 provides resistance to the flow of eddy currents in the conductive case of the IMD 100 that may be induced during recharge of the rechargeable battery 106. The cutout 110 further permits the slot antenna 112 disposed inside the IMD 100 to transmit and receive radio frequency signals. The transceiver 114 may be coupled to the slot antenna 112 and configured to provide radio frequency signals to the slot antenna 112 for transmission and to receive radio frequency signals from the slot antenna 112. In an exemplary embodiment, the transceiver 114 may include a transmitter and a receiver pair. The slot antenna 112 may be separated from the conductive case of the IMD 100 by a dielectric layer.

In some embodiments, the IMD 100 may be configured to transmit and receive radio frequency signals during recharging of the rechargeable battery 106. Further, the IMD 100 may be configured to transmit a radio frequency signal to the external charging device 120. The transmitted signal may be configured to provide information relating to the recharging of the rechargeable battery 106. The information may be used to notify the external charging device 120 that the rechargeable battery 106 is fully charged, to indicate that the temperature of the IMD 100 has exceeded a temperature tolerance level, to assist the external charging device 120 in determining the resonant frequency for recharging, or to provide another indication that may be useful during the recharging process. Providing feedback to the external charging device 120 may increase efficiency of the recharging process, reduce charging time, and increase safety.

Referring to FIGS. 2A and 2B, illustrations of various eddy currents are shown according to exemplary embodiments. In FIG. 2A, IMD 100 includes the header 104 and a conductive case 200. The conductive case 200 may be made from titanium, stainless steel, or any other suitable conductive material for use as an implantable device case. The conductive case 200 may be configured to house the various components of the IMD 100, such as the secondary coil 102 of FIG. 1, the rechargeable battery 106, the processor 108, and the slot antenna 112. During recharge of the rechargeable battery 106, the flow of eddy currents 202 and 204 may be induced in the conductive case 200 causing heating of the conductive case 200. Excessive heating of the conductive case 200 may result in damage to the surrounding tissue. The flow of eddy currents, and resulting heating of the conductive case 200, may be reduced by providing one or more cutouts in the conductive case 200, such as cutout 110 of FIG. 2B. The cutout 110 may be filled with a dielectric material, such as ceramic. The cutout 110 increases resistance to the flow of eddy currents in the conductive case 200, resulting in reduced flow of eddy currents 206 and 208. The increased resistance to the flow of eddy currents may reduce heating in the conductive case 200. A slot antenna, such as slot antenna 112 of FIG. 1, may be disposed within the conductive case 200 and aligned with the cutout 110 so that the slot antenna 112 may transmit and receive radio frequency signals.

Figure 3:
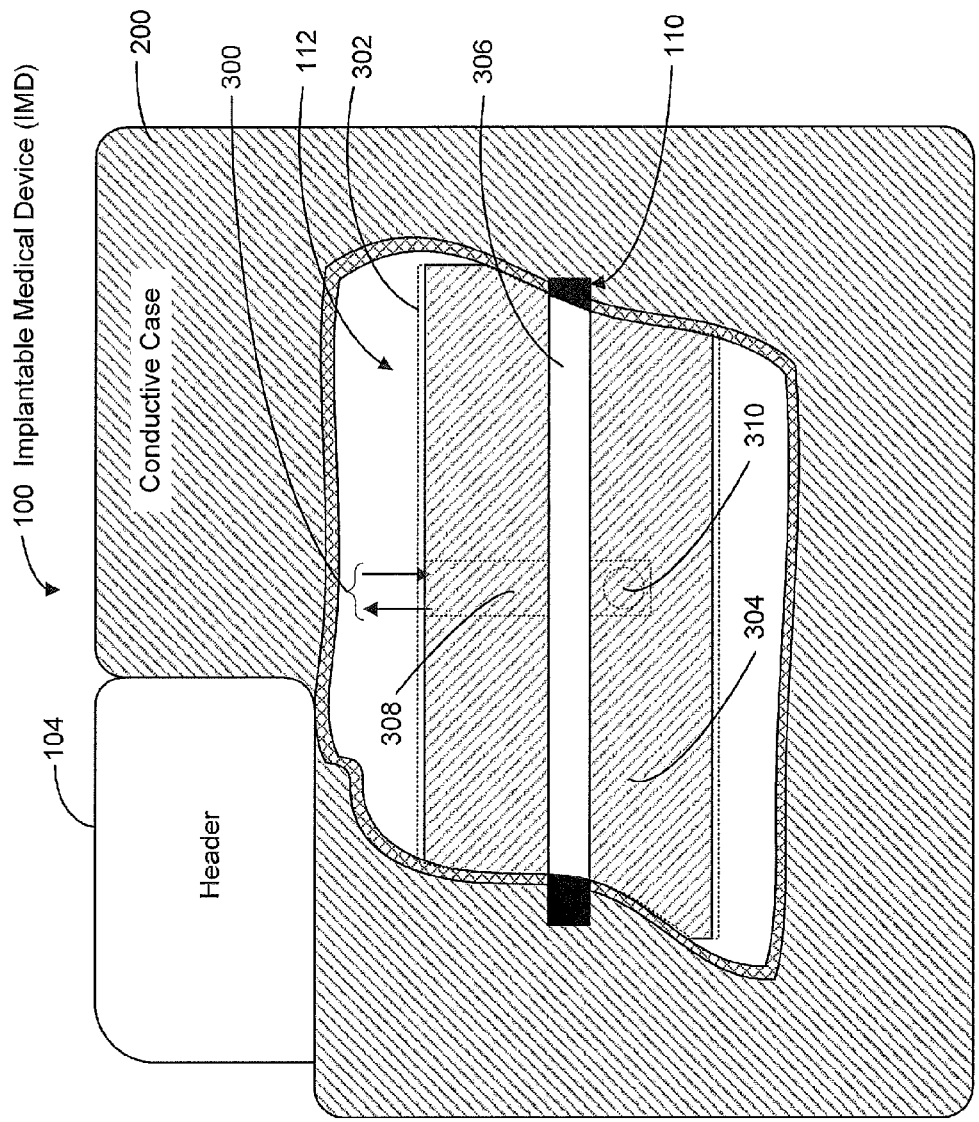
FIG. 3 is a diagram of an implantable medical device according to an exemplary embodiment.

Referring to FIG. 3, a diagram of an implantable medical device (IMD) 100 is shown according to an exemplary embodiment. The IMD 100 may include the conductive case 200, the header 104, the cutout 110 filled with a dielectric material, and the slot antenna 112 disposed within the conductive case 200. The slot antenna 112 may include a metal layer 304 and a slot 306 formed by removing a portion of the metal layer 304. A dielectric layer 302 may be provided between the conductive case 200 and the metal layer 304 including the slot 306. The dielectric layer 302 may be an insert provided on the inside wall of the conductive case 200 or may be formed on the metal layer 304 and the slot 306. The slot antenna 112 may further include a feed line 308 formed in a second metal layer and configured to communicate data 300 using radio frequency signals to and from the slot 306. The slot antenna 112 may include a port coupled to the feed line 308 to facilitate communication between a transceiver and the feed line 308. The feed line 308 may be shorted to the metal layer 304 using a conductive via 310. In another embodiment, instead of shorting the feed line 308 to the metal layer 304, the feed line 308 may include a feed (or stub) that creates a virtual short at certain frequencies as will be described further in FIG. 4B. The slot antenna 112 may be formed from a PC board having at least two metal layers. In another exemplary embodiment, the dielectric layer 302 may be formed over the metal layer 304 and the slot 306 using chemical vapor deposition (CVD), including plasma enhanced CVD and low-pressure CVD, atomic layer deposition (ALD), and physical layer deposition (PLD). Any other type of deposition process may be used to form the dielectric layer 302 without departing from the scope of the present disclosure.

Figure 4A:
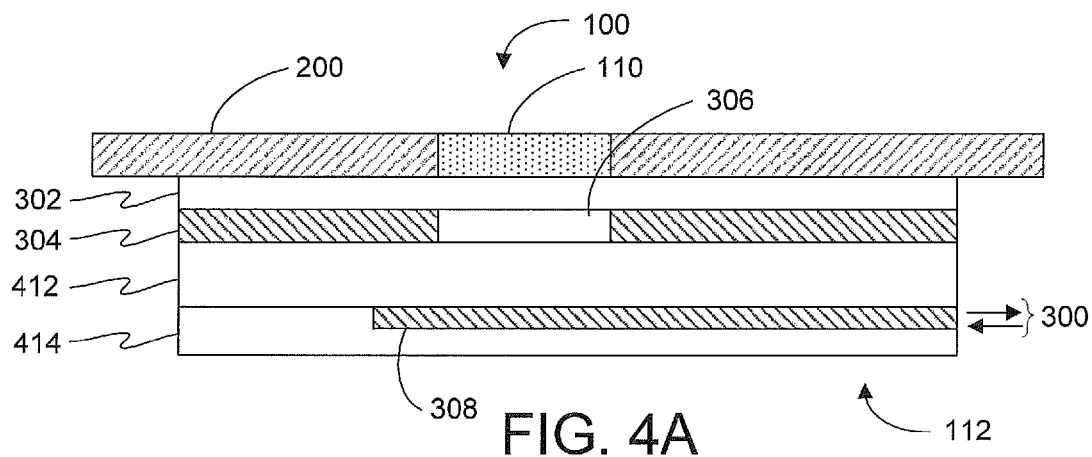
FIGS. 4A-4B illustrate a side view and a layering view of an implantable medical device according to an exemplary embodiment.
Figure 4B:
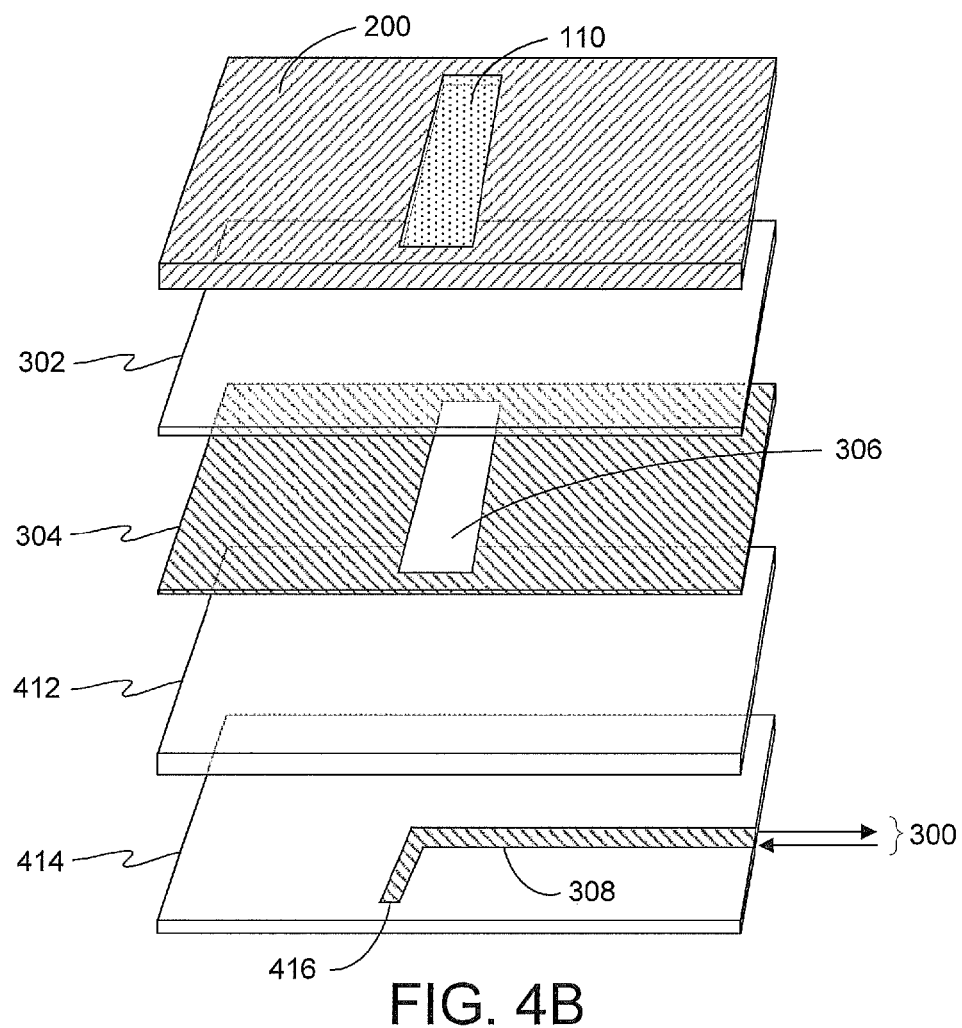

Referring to FIGS. 4A-4B, a side-view diagram of a portion of the IMD 100, including the slot antenna 112, is shown according to an exemplary embodiment. The IMD 100 includes a conductive case 200 having a cutout 110 filled with a dielectric material, such as ceramic material. The IMD 100 may be configured to house the slot antenna 112 having a slot 306 aligned with the cutout 110. The slot antenna 112 includes a metal layer 304 provided on a dielectric substrate 412. A portion of the metal layer 304 may be removed to form a slot 306. The slot 306 may be filled with a dielectric material or left empty.

A dielectric layer 302 may be provided between the conductive case 200 and the metal layer 304 including the slot 306. The dielectric layer 302 may be an insert provided on the inside wall of the conductive case 200 or it may be deposited, grown, or otherwise formed on the metal layer 304 and the slot 306. The slot antenna 112 may further include a feed line 308 formed as a second metal layer and configured to communicate data 300 using radio frequency signals to and from the slot 306. The feed line 308 may include a feed 416 (or stub) that creates a virtual short at certain frequencies. The feed 416 length may be sized to be equal to approximately one quarter of the wavelength (e.g., $\lambda/4$) of the radio frequency signals transmitted by the slot antenna 112; however, various other lengths may be used. The width and height of the feed line 308 and the feed 416 may be determined based on the impedance of the conductive material used.

While the feed 416 of FIG. 4B is at a ninety degree angle with respect to the feed line 308, the feed 416 may extend at other angles including one-hundred and eighty degrees from the feed line 308 to form a linear metal trace. In another embodiment, the slot antenna 112 may include at least a third metal layer, and the feed 416 may extend to the third metal layer using a conductive via. Further, the feed 416 may be extended to multiple metal layers using multiple conductive vias. The feed 416 may also form a T-shape with respect to the feed line 308. A dielectric layer 414 may be provided over the second metal layer including the feed line 308 to insulate the slot antenna 112 from other components housed within the IMD 100.

In some embodiments, the slot antenna 112 may be formed using a PC board having at least two conductive layers. The conductive layers, such as metal layer 304 and the second metal layer in which the feed line 308 is formed, may be made from copper. The dielectric substrate 412 may be selected from a variety of dielectric materials, including, but not limited to, Teflon, FR-1, FR-2, FR-3, FR-4, FR-5, FR-6, CEM-1, CEM-2, CEM-3, CEM-4, CEM-5, and G-10. In some embodiments, the dielectric substrate 412 may be a flexible plastic substrate used to form a flexible printed circuit. The flexible plastic substrate may be a polyimide material, polyether ether ketone (PEEK) material, or any other suitable material.

In some embodiments, the slot antenna 112 may be formed on a multi-layered PC board such that various electronic components used by the IMD 100 may be provided on one or more of the layers of the multi-layered PC board.

Figure 5A:
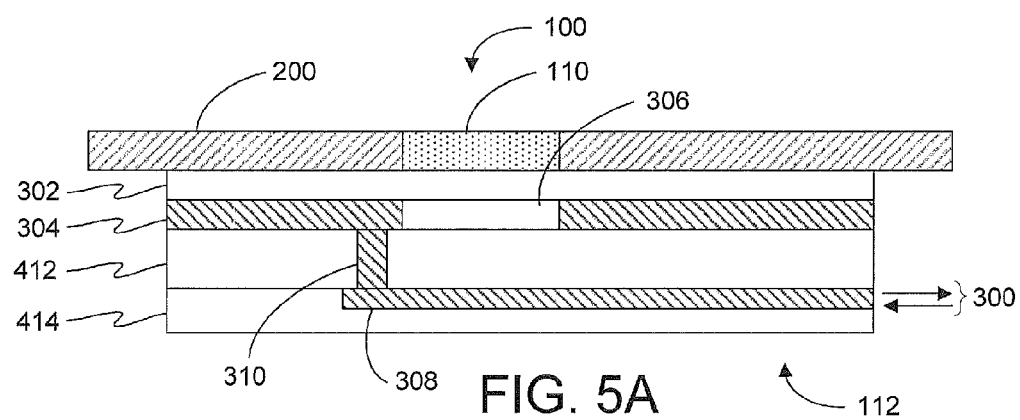
FIGS. 5A-5B illustrate a side view and a layering view of an implantable medical device according to an exemplary embodiment.
Figure 5B:
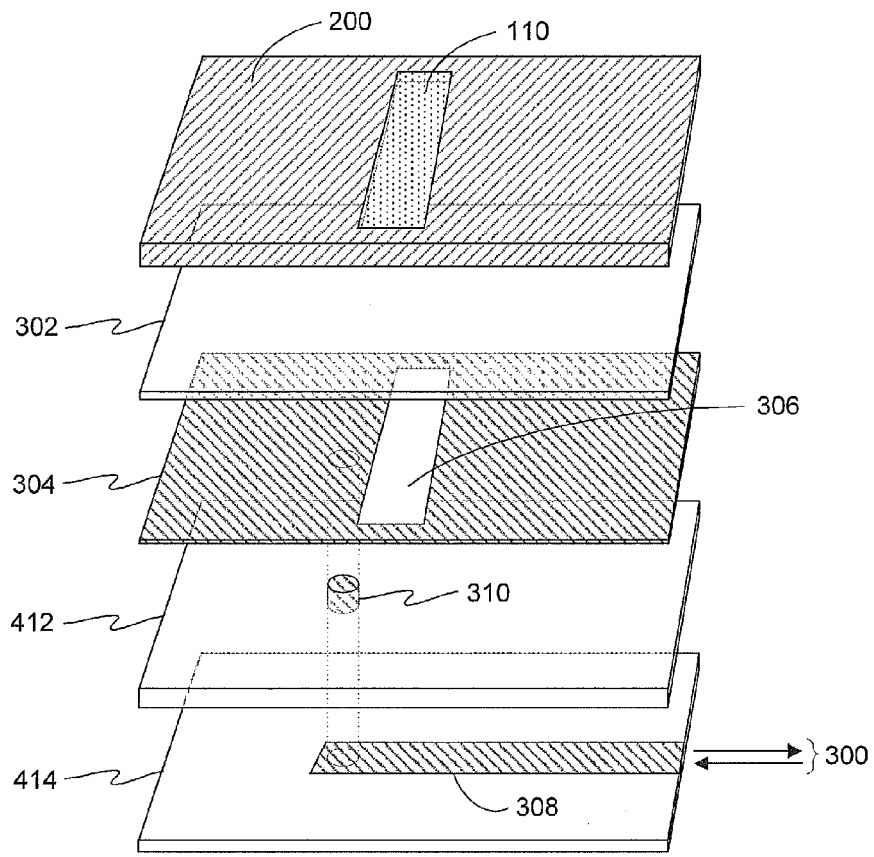

Referring to FIGS. 5A-5B, another side-view diagram of a portion of the IMD 100 is shown according to an exemplary embodiment. As previously described with respect to FIGS. 4A-4B, the IMD 100 may include a conductive case 200, a cutout 110 in the conductive case 200 filled with a dielectric material, a dielectric layer 302, a metal layer 304 including a slot 306 formed by removing a portion of the metal layer 304, a dielectric substrate 412, a feed line 308, and a dielectric layer 414. The feed line 308 may be configured to communicate data 300 using radio frequency signals to and from the slot 306. FIGS. 5A-5B further depict a conductive via 310 for coupling the feed line 308 to the metal layer 304. Coupling the feed line 308 to the metal layer 304 allows for a more compact design by eliminating the need to form a virtual short with the feed 416 (or stub) of FIG. 4B.

Figure 6A:
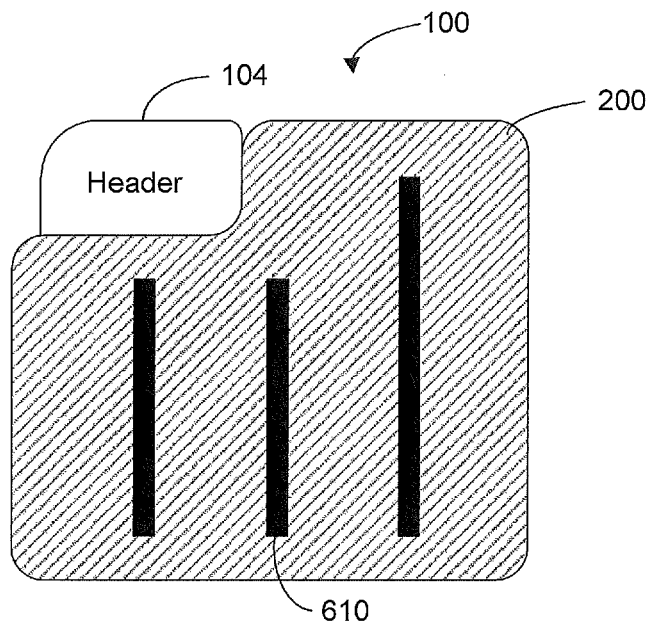
FIGS. 6A-6B illustrate an implantable medical device having multiple cutouts according to an exemplary embodiment.
Figure 6B:
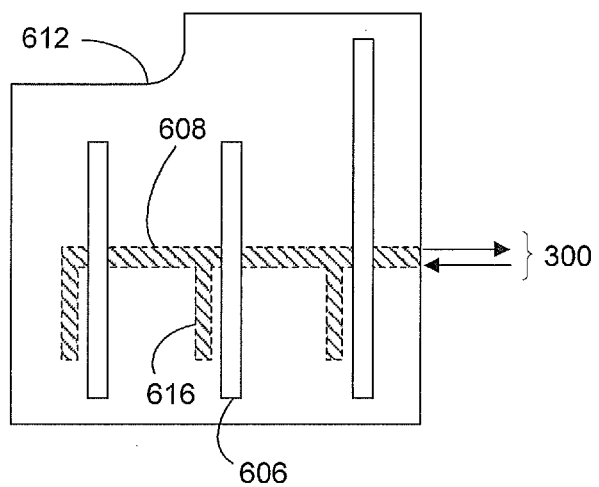

Referring to FIGS. 6A-6B, an IMD 100 having multiple cutouts 610 is shown according to an exemplary embodiment. The cutouts 610 in the conductive case 200 may be spaced apart to maximize the reduction of, or to further reduce, the flow of eddy currents. The cutouts 610 may be filled with a dielectric material, such as ceramic. A slot antenna 612 may be disposed within the conductive case 200 such that slots 606 of the slot antenna 612 are aligned with the cutouts 610. The slot antenna 612 may include the layers shown in FIGS. 4A-4B and 5A-5B. For simplicity, only the slots 606, the feed line 608, and feeds 616 are shown. The slots 606 may be formed by removing portions of a metal layer. The feed line 608 may be configured to communicate data 300 using radio frequency signals to and from the slots 606. The feed line 608 and the metal layer in which the slots 606 are formed are separated by a dielectric layer or substrate. The feed line 608 passes under each slot and may include feeds 616 which may be sized to have a length of approximately one quarter of the wavelength (e.g., λ/4) of the radio frequency signals transmitted by the slot antenna 612; however, various other lengths may be used. In some embodiments, one or more vias may be used to couple the feed line 608 to the metal layer in which the slots 606 are formed. Any number of cutouts 610 may be used. Further, the cutouts 610 may be any shape or design (e.g., curved, jagged, angled, tapered width) or form any pattern including a radial pattern.

Referring to FIGS. 7A-7C, another implantable medical device 100 having multiple cutouts 710 is shown according to an exemplary embodiment. The cutouts 710 in the conductive case 200 form a radial pattern. In some embodiments, the radial pattern may be located in a center or an off-center location. Further, the radial pattern may be centered on the portion of the conductive case 200 covering the secondary coil 102 of FIG. 1. The cutouts 710 may be filled with a dielectric material, such as ceramic. In some embodiments, the number of cutouts 710, and corresponding slots 706, forming the radial pattern may be fewer than six, while in other embodiments there may be more than six cutouts 710 and corresponding slots 706 in the radial pattern. A feed line 708 may be configured to communicate data 300 using radio frequency signals to and from the slots 706. A slot antenna 712 may be disposed within the conductive case 200 such that slots 706 of the slot antenna 712 are aligned with the cutouts 710. The slot antenna 712 of FIGS. 7B-7C may include the layers shown in FIGS. 4A-4B and 5A-5B. For simplicity, only the slots 706, the feed line 708, and feeds 716 are shown. The slots 706 may be formed by removing portions of a metal layer, such as metal layer 304. The feed line 708 and the metal layer, in which the slots 706 are formed, are separated by a dielectric layer or substrate. The feed line 708 passes under the slots to form a circular pattern and may include the feeds 716 which may be sized to have a length of approximately one quarter of the wavelength (e.g., 214) of the radio frequency signals transmitted by the slot antenna 712; however, various other lengths may be used. In some embodiments, one or more vias may be used to couple the feed line 708 to the metal layer in which the slots 706 are formed. The feed line 708 of FIG. 7B may be used to both transmit and receive the data 300.

In some embodiments, a feed line 720 of FIG. 7C may be used to transmit data 300 while a feed line 718 may be used to receive data 300. The feed lines 720 and 718 each form a semi circular pattern. The feed line 720 may include feeds 722 configured for transmitting data 300. In some embodiments, one or more of the feeds 722 may be replaced with conductive vias, such as the conductive via 310 of FIGS. 5A-5B. The feed line 718 may include feeds 724 configured for receiving data 300. In some embodiments, one or more of the feeds 724 may be replaced with conductive vias, such as the conductive via 310 of FIGS. 5A-5B.

Further, the cutouts 710, and corresponding slots 706, may be any shape or design (e.g., curved, jagged, angled, tapered width, U-shaped, L-shaped, T-shaped, dog bone shaped). The length of each of the slots 706 need not be the same. The slots 706 need not be as long as the cutouts 710 or the same width.

Figure 8:
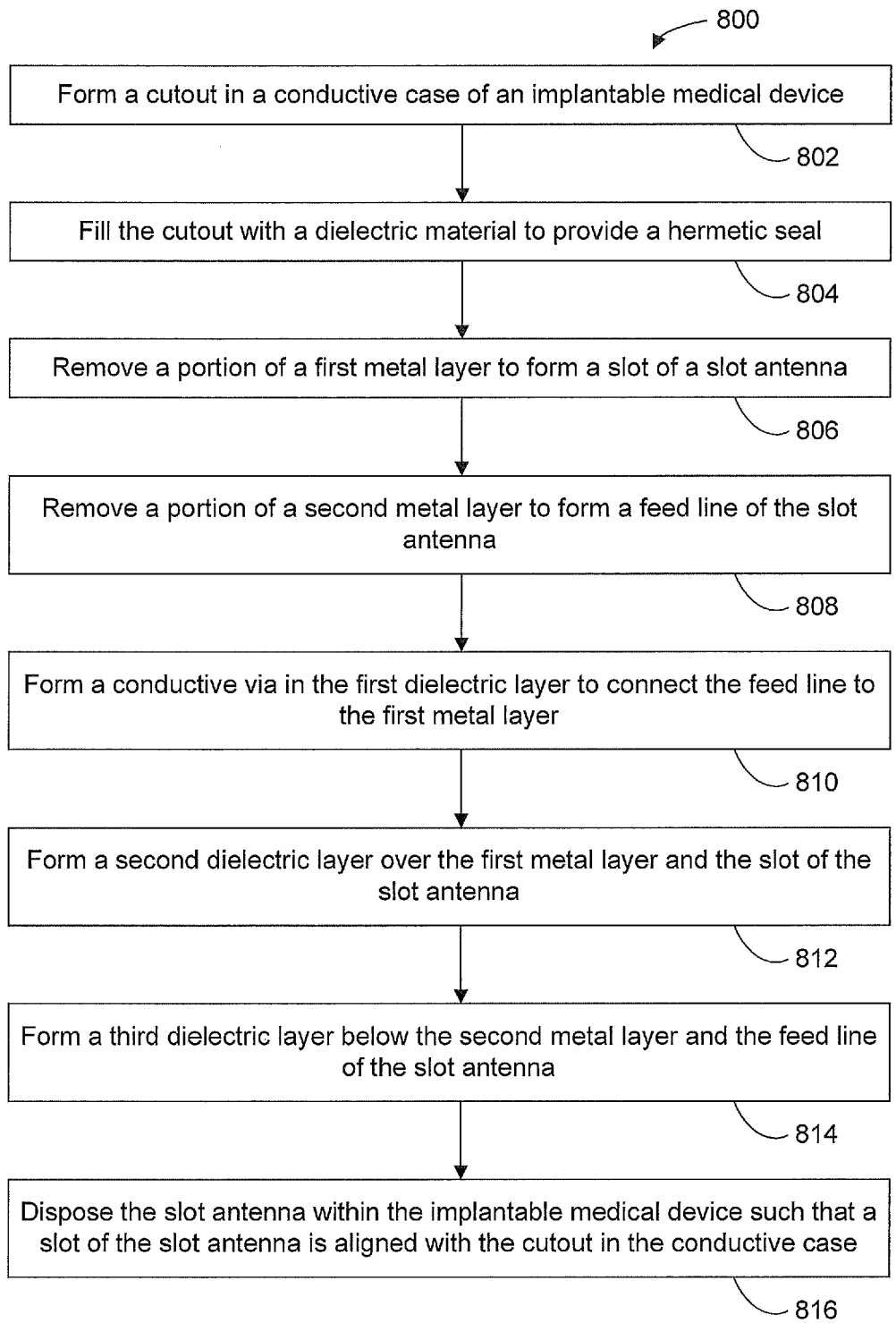
FIG. 8 is a flow chart for a method of manufacturing an implantable medical device according to an exemplary embodiment.

Referring to FIG. 8, a process flow chart for a method 800 of manufacturing an implantable medical device is shown according to an exemplary embodiment. The method 800 may include forming a cutout in a conductive case of an implantable medical device, at 802. The case may be made from a metallic material, such as titanium or stainless steel. In an alternative embodiment, the case may be non-metallic. The method 800 may also include filling the cutout with a dielectric material to provide a hermetic seal, at 804. The dielectric material may be a ceramic material or any other dielectric material suitable to form a hermetic seal. The method 800 may include removing a portion of a first metal layer to form a slot of a slot antenna, at 806. In an exemplary embodiment, the first metal layer may be disposed above a first dielectric layer or substrate. The first metal layer may be made from copper. The method 800 may include removing a portion of a second metal layer to form a feed line of the slot antenna, at 808. In an exemplary embodiment, the second metal layer may be disposed below the first dielectric layer or substrate and may also be made from copper. The method 800 may also include forming a conductive via in the first dielectric layer to connect the feed line to the first metal layer, at 810. The method 800 may include forming a second dielectric layer over the first metal layer and the slot of the slot antenna, at 812. The method 800 may include forming a third dielectric layer below the second metal layer and the feed line of the slot antenna, at 814. The method 800 may include disposing the slot antenna within the implantable medical device such that the slot of the slot antenna is aligned with the cutout in the implantable medical case, at 806. In an exemplary embodiment, the first metal layer in which the slot is formed may not be in contact with the conductive case.

Figure 9:
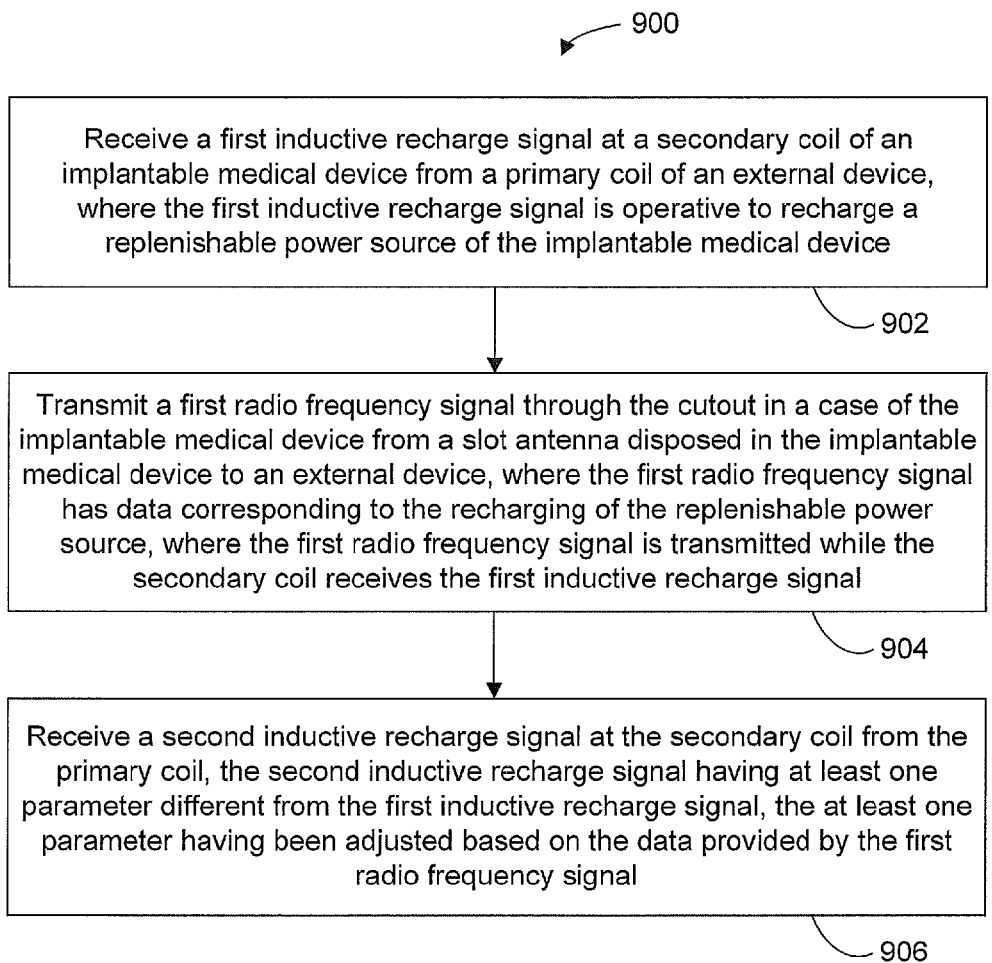
FIG. 9 is a flow chart for a method of communicating via a slot antenna during a recharging process according to an exemplary embodiment.

Referring to FIG. 9, a process flow chart for a method 900 of communicating via the slot antenna during a recharging process is shown according to an exemplary embodiment. The method 900 may include receiving a first inductive recharge signal at a secondary coil of the implantable medical device from a primary coil of an external device, at 902. In an exemplary embodiment, the first inductive recharge signal may be operative to recharge a replenishable power source of the implantable medical device, such as a rechargeable battery. The method 900 may also include transmitting a first radio frequency signal through a cutout in a case of the implantable medical device from a slot antenna disposed in the implantable medical device to an external device, at 904. In an exemplary embodiment, the first radio frequency signal transmits or encodes data corresponding to the charging of the replenishable power source, and the first radio frequency signal may be transmitted while the secondary coil receives the first inductive recharge signal. The method 900 may include receiving a second inductive recharge signal at the secondary coil from the primary coil, where the second inductive recharge signal has at least one signal parameter that is different from a corresponding signal parameter of the first inductive recharge signal, the at least one signal parameter of the second inductive recharge signal having been adjusted based on the data provided by the first radio frequency signal, at 906. In this manner, a recharging feedback loop may be provided to the external charging device to maintain safety and efficiency during the recharging process. In an exemplary embodiment, the recharging feedback loop may be utilized to monitor the recharging process to maintain the temperature of the any portion of the implantable medical device. In some embodiments, the recharge feedback loop may be used to determine the resonant frequency for the recharge process and to assist in maintaining the inductive recharge signal at or near the resonant frequency during the recharge process.

Using the data provided by the recharging feedback loop, the external recharging device may be configured to monitor the effects of the inductive recharging signal on the implantable medical device and its components and to adjust the inductive recharging signal to improve the safety and efficiency of the recharge process. In an exemplary embodiment, the external recharging device may be configured to monitor a temperature of the implantable medical device and to adjust the parameters of the inductive recharging signal based on the temperature. For example, the external recharging device may attempt to reduce the temperature of the implantable medical device by discontinuing the recharge process, reducing the duty cycle of the inductive recharge signal, adjusting the frequency of the inductive recharge signal to more closely match the resonant frequency, and reducing the magnitude of the inductive recharge signal. The external recharging device, or any other external computing device configured to communicate with the implantable medical device, may use the data to generate a status report or a history report of the implantable medical device. The status report and/or history report may include temperature data, frequency data, or any other data provided by the implantable medical device. The external recharging device, or any other external computing device configured to communicate with the implantable medical device, may also be configured to generate a recharging request based on the monitoring of the implantable medical device. For example, the external device may notify the user that a power level of the rechargeable battery has dropped below a power threshold and is in need of recharging.

In the following description, "over," "under," "behind," "beneath" and similar terms are used to denote relative positions of particular components or elements when an implantable medical device (IMD) is in a particular orientation (e.g., a side view orientation depicted in FIG. 12), and such terms do not denote an absolute position of the particular components or elements. For example, as used herein, a first component of the IMD is "over" a second component when the IMD is in the side view orientation depicted in FIG. 12 and the first component is closer to a top surface of the IMD (i.e., a first surface 1220 of an IMD 1000 in FIG. 12) than the second component. Obviously, the IMD could be turned over such that positions of the first surface 1220 and a second surface 1222 of FIG. 12 were reversed without changing the physical arrangement of the first and second components. As the term is used herein, the first component would still be "over" the second components despite reversing or otherwise changing the orientation of the IMD 1000 since the terms are defined relative to the particular orientation of the IMD 1000 illustrated in FIG. 12. Thus, for consistency and for ease of description, relative positions of the components of IMDs are defined and described herein with reference to the orientation illustrated in FIG. 12.

Figure 10:
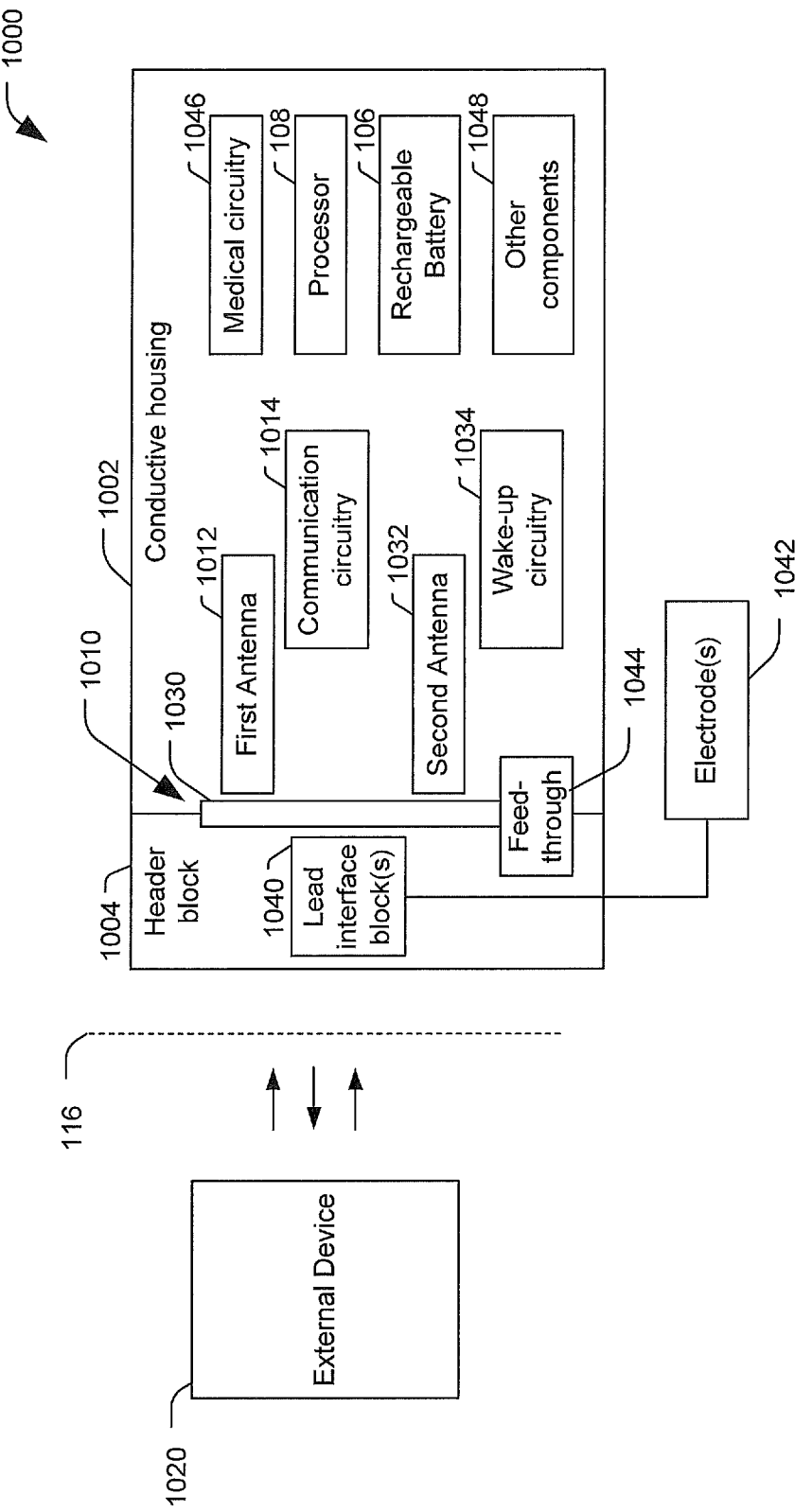
FIG. 10 is a block diagram of an implantable medical device and an external charging device according to a particular embodiment.

FIG. 10 is a block diagram of an implantable medical device (IMD) 1000 and an external device 1020 according to a particular embodiment. The IMD 1000 may have features and functions in common with the IMD 100 of FIG. 1. For example, the IMD 1000 may be implanted within a patient behind the tissue barrier 116 of the patient (e.g., the patient's skin and/or other tissue). In a particular embodiment, the IMD 1000 includes the rechargeable battery 106. In another embodiment, the IMD 1000 includes a different power source, e.g., a non-rechargeable battery. The IMD 1000 may also include the processor 108. The processor 108 may be operable to control processes of the IMD 1000, such as recharging of the battery, sensing or stimulation provided by medical circuitry 1046, communication performed by communication circuitry 1014, changing states of components of the IMD 1000 in response to wake-up circuitry 1034, other processes performed by other components 1048 of the IMD 1000, or any combination thereof.

The IMD 1000 may also include a conductive housing 1002 that defines an opening 1010. The conductive housing 1002 may be formed of a biocompatible material, such as a metal or metal alloy (e.g., Titanium or stainless steel). The IMD 1000 may also include one or more antennas, such as a first antenna 1012 and a second antenna 1032 that are hermetically sealed within the conductive housing 1002.

A dielectric material 1030 may be coupled to the conductive housing 1002 to hermetically seal the opening 1010. Together, the dielectric material 1030 and the conductive housing 1002 form a case of the IMD 1000. The dielectric material 1030 may include a ceramic material, a polymer material or another dielectric material that is suitable to form a hermetic seal with the conductive housing 1002. Hermetic seals between polymers and metals, such as the conductive housing 1002, can be less reliable than hermetic seals between ceramics and metals. When the dielectric material 1030 is a ceramic, the hermetic seal may be formed via a ceramic-to-metal sealing process, such as brazing or welding. One or more of the antennas 1012, 1032 may be positioned within the case behind the dielectric material 1030. Without the opening 1010, the conductive housing 1002 may interfere with communication between an external device 1020 and the first antenna 1012, the second antenna 1032, or both. The opening 1010 hermetically sealed by the dielectric material 1030 provides a signal path through the conductive housing 1002, which results in significantly less signal strength reduction than would be experienced by attempting to transmit through the conductive housing 1002.

The IMD 1000 may include a header block 1004. The header block 1004 may be coupled to the case over the dielectric material 1030. When the dielectric material 1030 is formed of a relatively brittle material, such as ceramic, the header block 1004 may be configured to retain pieces of the dielectric material 1030 in an event of a catastrophic failure of the dielectric material 1030. For example, the header block 1004 may be formed of a first material that has a first mechanical failure mechanism (e.g., plastic deformation) when implanted within a patient, and the dielectric material 1030 may be formed of a second material that has a second mechanical failure mechanism (e.g., shattering) when implanted within the patient. The second material may be more brittle at body temperature than the first material. Thus, the header block 1004 may protect the dielectric material 1030 against catastrophic failure by absorbing impact energy that would otherwise be absorbed by the dielectric material 1030, potentially leading to shattering of the dielectric material. Additionally, the header block 1004 may be coupled to the conductive housing 1002 in a manner that causes the header block 1004 to prevent pieces of the dielectric material 1030 from being exposed to tissue of the patient. For example, the header block 1004 may be coupled to the conductive housing 1002 via a press fit, via one or more connectors (e.g., screws, rivets or snaps), via an adhesive, or via another polymer to metal joining process or technique.

The header block 1004 may include lead interface blocks 1040. The lead interface blocks 1040 may be adapted to receive one or more electrode leads from electrodes 1042. The lead interface blocks 1040 may be coupled to the medical circuitry 1046 within the conductive housing 1002 via one or more hermetically sealed feedthroughs 1044. The electrodes 1042 may include stimulation electrodes, sensing electrodes, or a combination thereof. Likewise, the medical circuitry 1046 may include therapeutic circuitry, sensing circuitry, or a combination thereof. In a particular embodiment, as further illustrated in FIG. 11, one or more of the lead interface blocks 1040 may at least partially obscure one or more of the antennas 1012, 1032. Accordingly, one or more of the lead interface blocks 1040 may be formed of a material that is suitable to provide electrical connection between the medical circuitry 1046 and the electrodes 1042, but does not significantly reduce signal strength of signals transmitted between the external device 1020 and the particular antenna or antennas 1012, 1032 that may be partially obscured by the lead interface blocks 1040. For example, the lead interface blocks 1040 may be formed of stainless steel (e.g., 316L stainless steel), MP35N, or Titanium. In another embodiment, the lead interface blocks 1040, the antennas 1012, 1032 may be positioned to limit interference of the lead interface blocks 1040 with signals transmitted between the external device 1020 and the antennas 1012, 1032.

The IMD 1000 may include communication circuitry 1014 within the case and coupled to the first antenna 1012. The communication circuitry 1014 may be operable to send signals to a device external to the conductive housing 1002, such as the external device 1020, to receive signals from the device external to the conductive housing 1002, or both send and receive signals. For example, the communication circuitry 1014 may be operable to transmit data to the external device 1020. The transmitted data may include data gathered by medical circuitry in response to conditions detected by the electrodes 1042 or data generated by the processor, such as data related to therapy provided to the patient or data related to a condition of the IMD (e.g., a charge state of the rechargeable battery 106, a case temperature of the IMD 1000, or functionality of a component of the IMD 1000). In another example, the communication circuitry 1014 may be operable to receive data from the external device 1020. The received data may include stimulation therapy parameters, activation signals to activate one or more of the other components 1048 of the IMD 1000, other data, or a combination thereof.

The IMD 1000 may include wake-up circuitry 1034 within the conductive housing 1002. The wake-up circuitry 1034 may be coupled to the second antenna 1032. The wake-up circuitry 1034 may be operable, in response to a wake-up signal received at the second antenna 1032, to cause the communication circuitry 1014 to transition from a sleep state in which the communication circuitry 1014 is inactive to an awake state in which the communication circuitry 1014 is active. In a particular embodiment, the wake-up circuitry 1034 may awaken another or a different component of the IMD 1000 in response to the wake-up signal. For example, the communication circuitry 1014, the processor 108, the medical circuitry 1046, one or more of the other components 1048, or a combination thereof, may transition to a sleep state at particular times to conserve power or for other purposes. The wake-up signal may be used to awaken any component of the IMD 1000 to which the wake-up signal is directed. To illustrate, the communication circuitry 1014 may enter the sleep state when no communication has been received from the external device 1020 for a particular period of time. To awaken the communication circuitry 1014 (e.g., to transmit a new therapy program to be implemented by the IMD 1000), the external device 1020 may first transmit the wake-up signal and wait for an acknowledgement from the communication circuitry 1014 indicating that the communication circuitry 1014 is in the active state before transmitting additional data.

In a particular embodiment, the first antenna 1012 is a planar antenna. Use of a planar antenna may be beneficial where available space is constrained, such as within the conductive housing 1002. For example, the first antenna 1012 may include one or more conductive elements disposed on a circuit board. To illustrate, the first antenna 1012 may be a loop or coil-type antenna disposed on the circuit board. In another illustrative example, the first antenna 1012 may be a slot-type antenna including a conductive layer on a surface of the circuit board. The conductive layer may define a radiating slot. For example, the first antenna 1012 may be formed as described with reference to FIGS. 4A and 4B.

In a particular embodiment, the second antenna 1032 may be arranged to receive the wake-up signal through the first antenna 1012. To illustrate, when the first antenna is a slot-type antenna, the wake-up signal may propagate through the opening 1010 and through the radiating slot of the first antenna 1012 to be received by the second antenna 1032. Thus, space within the IMD 1000 may be further conserved by positioning the second antenna 1032 in an open area of the first antenna 1012, allowing both the first antenna 1012 and the second antenna 1032 to transmit and/or receive signals through the opening 1010 and the dielectric material 1030.

Figure 11:
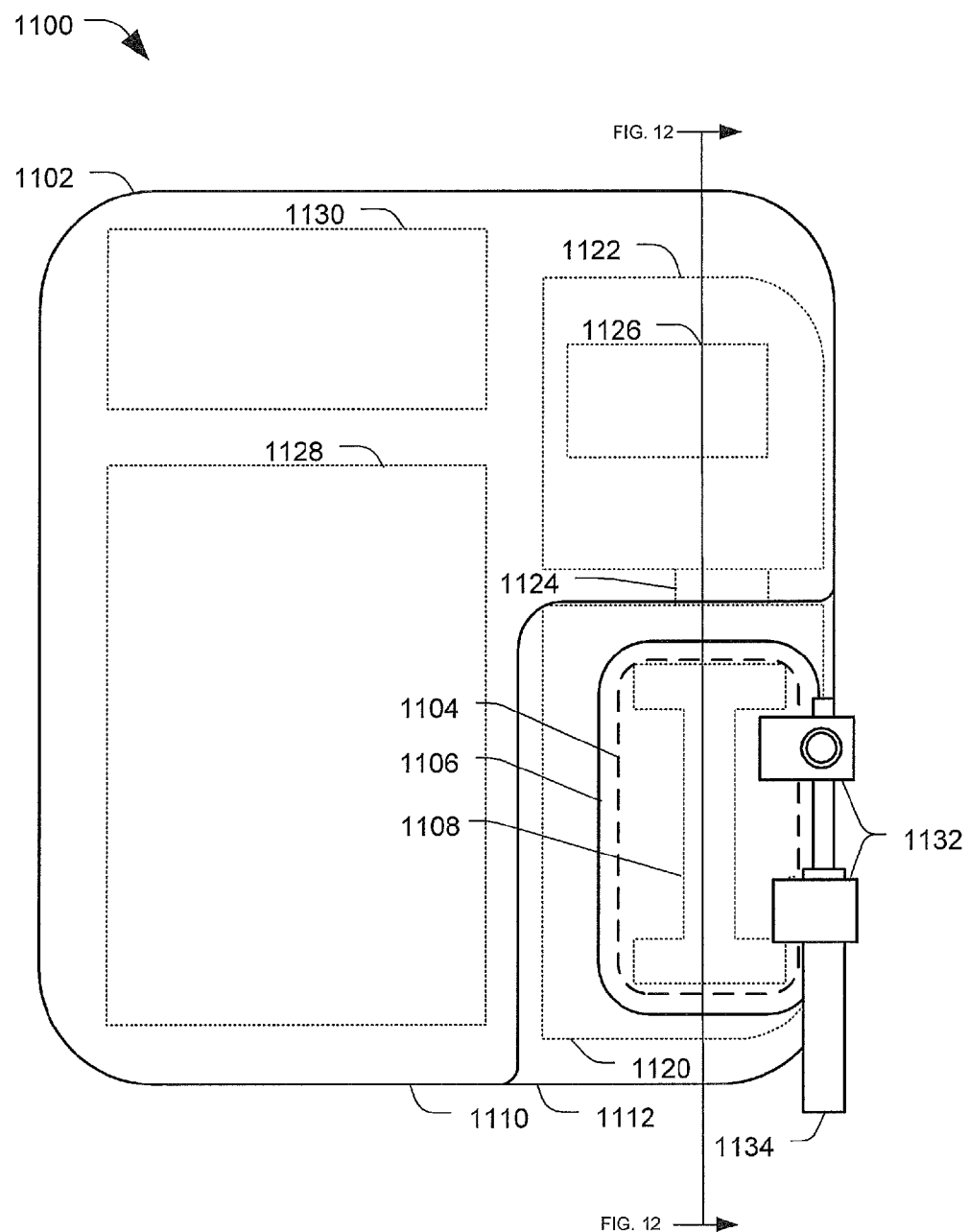
FIG. 11 is a schematic illustration of a top view of an implantable medical device with a header block removed according to a particular embodiment.
Figure 12:
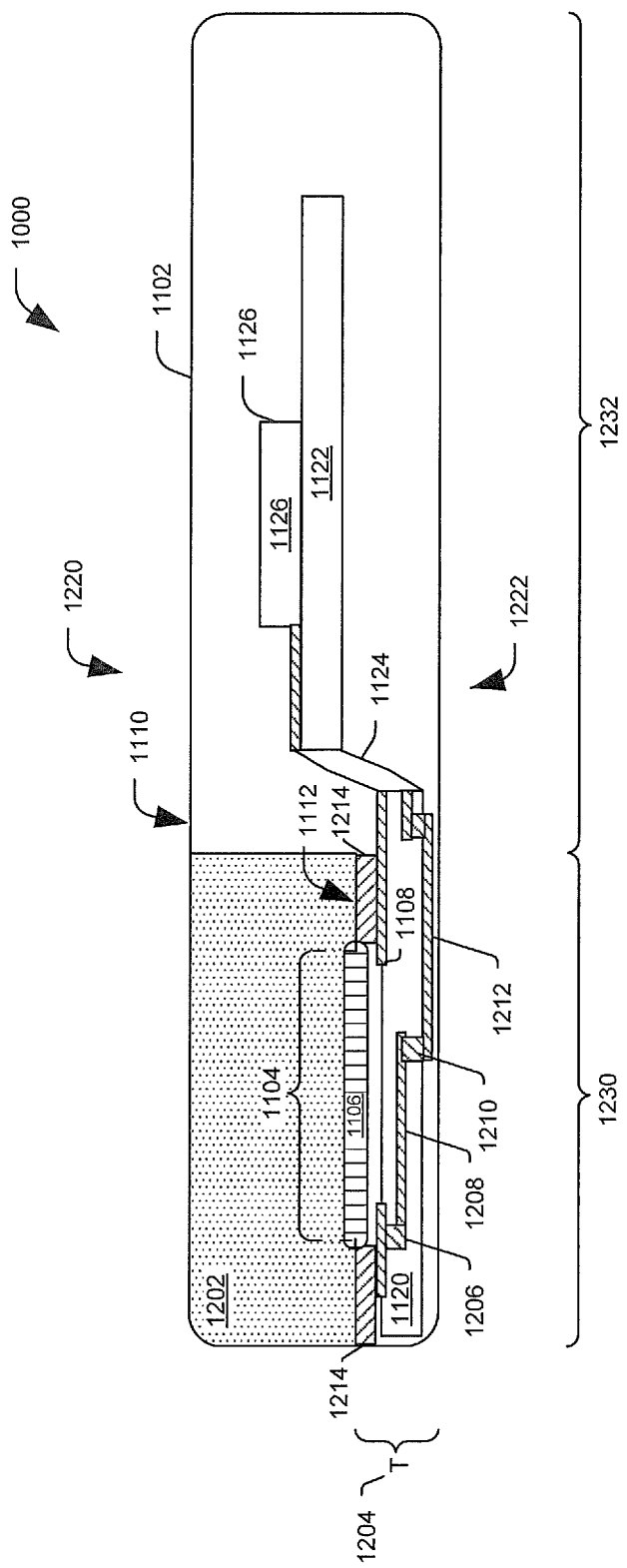
FIG. 12 is a schematic illustration of a cutaway side view of an implantable medical device according to a particular embodiment.

FIG. 11 is a schematic illustration of a top view of an implantable medical device (IMD) 1100. FIG. 12 is a cutaway side view of the IMD 1100 along a section line shown in FIG. 11. In the view depicted in FIG. 11, components internal to a conductive housing 1102 of the IMD 1000 are shown in dotted lines. Additionally, while FIG. 12 shows a header block 1202, the header block 1202 is not shown in FIG. 11.

The IMD 1100 includes a power source, such as a battery 1128. For example, the battery 1128 may be a rechargeable battery, such as the rechargeable battery 106 of FIG. 1 and FIG. 10. The IMD 1100 may also include functional circuitry 1130 such as medical circuitry (e.g., therapeutic circuitry, sensing circuitry or both), a processor, memory, charging circuitry, other components or a combination thereof. The medical circuitry of the functional circuitry 1130 may be coupled to one or more lead interface blocks 1132 external to the conductive housing 1102 via one or more hermetically sealed feedthroughs (not shown in FIG. 11). The lead interface blocks 1132 may be adapted to receive an electrode lead 1134. The electrode lead 1134 may be coupled to an electrode (not shown in FIG. 11) that is coupled to or positioned proximate to tissue of a patient that is to be stimulated or from which data is to be sensed.

The IMD 1100 may also include communication circuitry 1126. For example, the communication circuitry 1126 may include a receiver, a transmitter, a transceiver, a coder/decoder (CODEC), other components that operate to facilitate communication between the IMD 1100 and a device external to the patient, or a combination thereof. The communication circuitry 1126 may be coupled to one or more antennas, such as an antenna 1108. Other examples of antennas and communication circuitry are described with reference to FIGS. 13A-13E.

In a particular embodiment, the conductive housing 1102 of the IMD 1100 may be hermetically sealed. The conductive housing 1102 may define an opening 1104 which may be hermetically sealed with a dielectric material 1106. For example, the dielectric material 1106 may fill the opening 1104 and extend past edges of the opening 1104 to form a seal with the conductive housing 1102. In a particular embodiment, the dielectric material 1106 is a ceramic material that is sealed to the conductive housing 1102 using a ceramic-to-metal brazing or welding process.

The antenna 1108 may be positioned within the conductive housing 1102 behind the dielectric material 1106. In a particular embodiment, at least one dimension of the opening 1104 (e.g., a length, a width, or both) is larger than a corresponding dimension of a radiating element of the antenna 1108. For example, in the particular embodiment illustrated in FIG. 11, the antenna 1108 is a slot-type antenna and the radiating element is shown as an "I" shape cutout of a conductive layer. Thus, at least one dimension of the opening 1104 may be larger than a corresponding dimension of the "I" shaped cutout in the conductive layer.

For ease of implantation in a patient and for comfort of the patient, it may be desirable for the IMD 1100 to have a relatively small form factor. Accordingly, the header block 1202 (in FIG. 12) may be positioned within a recess of the conductive housing 1102. To illustrate, as shown in FIG. 12, the conductive housing 1102 has a first side 1220 and a second side 1222 opposite the first side 1220. The first side 1220 may have a recessed portion 1112 (under the header block 1202) and a non-recessed portion 1110. A distance between non-recessed portion 1110 and the recessed portion 1112 of the first side 1220 is smaller than a second distance between the second side 1222 and the non-recessed portion 1110 of the first side 1220 by a thickness, T, 1204. The header block 1202 may extend from the recessed portion 1112 of the first side 1102 to approximately flush with the non-recessed portion 1110 of the first side 1102, thus providing a relatively small form factor such that the header block 1202, which houses the lead interface blocks 1132, blends relatively smoothly with the conductive housing 1102. The antenna 1108 may be positioned between the second side 1222 and the recessed portion 1112 of the first side 1220 in a first region 1230 with the thickness T 1204. Other components of the IMD 1000 may be positioned in a second region 1232 with a thickness greater than the thickness T 1204.

To enable the antenna 1108 to fit in the first region 1230, the antenna 1108 may be relatively thin, such as a planar antenna. In a particular embodiment, the antenna 1108 is formed on a first circuit board 1120 that can be positioned in the first region 1230 by sliding the first circuit board 1120 (or a portion of the first circuit board 1120) into the first region 1230. To simplify assembly of the IMD 1000, the communication circuitry 1126 may be coupled to a second circuit board 1122 that is communicatively coupled to the first circuit board 1120 via a flexible circuit 1124. Various configurations of the first circuit board 1120, the second circuit board 1122 and the flexible circuit 1124 are illustrated in FIGS. 13A-13E.

In a particular embodiment, circuitry that supports the antenna 1108 may also be formed on or coupled to the first circuit board 1120. For example, the first circuit board 1120 may include multiple layers. The antenna 1108 may include a conductive layer formed on or coupled to an upper surface (in the orientation depicted in FIG. 12) of the circuit board 1120. A feed line 1208 may be formed on the upper surface of the circuit board 1120, on a lower surface of the circuit board 1120 or between layers of the circuit board 1120 (e.g., interior to the circuit board 1120). When the feed line 1208 is on a different layer of the circuit board 1120 than the antenna 1108, the feed line 1208 may be coupled to the antenna 1108 by a conductive via 1206. Other components that support functionality of the antenna 1108 may also be formed on or coupled to the circuit board 1120, such as matching components 1212. The matching components 1212 may include inductive elements, capacitive elements or other elements that facilitate impedance matching of the antenna 1108, the feed line 1208 and other communication components, such as the communication circuitry 1126. When the feed line 1208 and the matching components 1212 are on different layers of the circuit board 1120, the matching components 1212 may be coupled to the feed line 1208 by a conductive via 1210.

In a particular embodiment, an insulating layer 1214 may be positioned between the antenna 1108 and an interior of the conductive housing 1102 in at least the first region 1230. The insulating layer 1214 may inhibit or prevent the antenna 1108 from shorting out against the conductive housing 1102. In a particular embodiments, the dielectric material 1106 may extend into the conductive housing 1102 such that the antenna 1108 is prevented from contacting the conductive housing 1102 by the dielectric material 1106. The insulating layer 1214 may not be present in this embodiment.

Positioning the antenna 1108 within the conductive housing 1102, as opposed to external to the conductive housing 1102, enables elimination of connective elements to connect the antenna 1108 to the communication circuitry 1126. Such connective elements tend to be bulky, failure prone and difficult to work with during manufacturing of an IMD. The conductive housing 1102 may reduce performance of the antenna 1108 when the antenna 1108 is positioned within the conductive housing 1102. Providing the opening 1104 that is hermetically sealed with the dielectric material 1106 reduces or eliminates interference of the conductive housing 1102 with communications via the antenna 1108. The header block 1202 protects the dielectric material 1106 from damage and protects the patient from pieces of the dielectric material 1106 in the event of catastrophic failure of the dielectric material 1106. Thus, effective communications may be provided safely, at low manufacturing cost, and in a relatively small form factor IMD 1000 by positioning the antenna 1108 within the conductive housing 1102 beneath the dielectric material 1106 and the header block 1202.

FIGS. 13A-13E are schematic illustrations of antenna systems for use inside an implantable medical device (IMD) according to various embodiments. The antenna systems illustrated in FIGS. 13A-13E each use a two circuit board configuration with the antenna 1108 on the first circuit board 1120 and the communication circuitry 1126 on the second circuit board 1122. The first circuit board 1120 may be coupled to the second circuit board 1122 by the flexible circuit 1124. Other configurations of the antenna 1108 and the communication circuitry 1126 may be used, such as the antenna 1108 and the communication circuitry 1126 on a single circuit board, the communication circuitry 1126 distributed across two or more circuit boards, or coupling the communication circuitry 1126 to the antenna 1108 using discrete wires rather than the flexible circuit 1124. Thus, in FIGS. 13A-13E, the two circuit board configuration is used in order to better highlight other differences between the illustrated embodiments.

In a particular embodiment, at least the first circuit board 1120 may have multiple layers. Portions of or components of the antenna system may be formed on or positioned on different layers of the first circuit board 1120. FIGS. 13A-13E are illustrated as top views of the various embodiments of the antenna system with components on a top layer depicted with solid lines, components on a middle or interior layer depicted with dashed lines, and components on a bottom layer depicted with dotted lines. The particular arrangements of components on layers of the first circuit board 1120 depicted in FIGS. 13A-13E are only illustrative and other arrangements are envisioned. For example, to save manufacturing cost, all components of the antenna system may be located on exterior surfaces of the circuit boards 1120, 1122, with no components located on the middle or interior layers. Additionally, in FIGS. 13A-13E, the antenna 1108 is illustrated as a slot-type antenna including a conductive layer 1302 on the top surface of the first circuit board 1120, where the conductive layer 1302 defines a radiating slot with an "I" shape. Other antenna configurations may be used. For example, other types of planar antenna may be used rather than a slot-type antenna, such as a dipole antenna, an inverted F antenna, a loop antenna, a coil antenna, a microstrip or patch antenna. Additionally, when a slot-type antenna is used, other shapes of the radiating slot may be used, such as one or more rectangular slots, a bow tie slot, an inverted "E" shaped slot, or another slot optimized for performance for a particular configuration of the IMD. The planar antennas may include conductive elements disposed on the first circuit board 1120. A non-planar antenna may also be used so long as the non-planar antenna is configured to be positioned within a conductive housing of an IMD beneath an opening in the conductive housing (as described with reference to FIGS. 11 and 12).

Figure 13C:
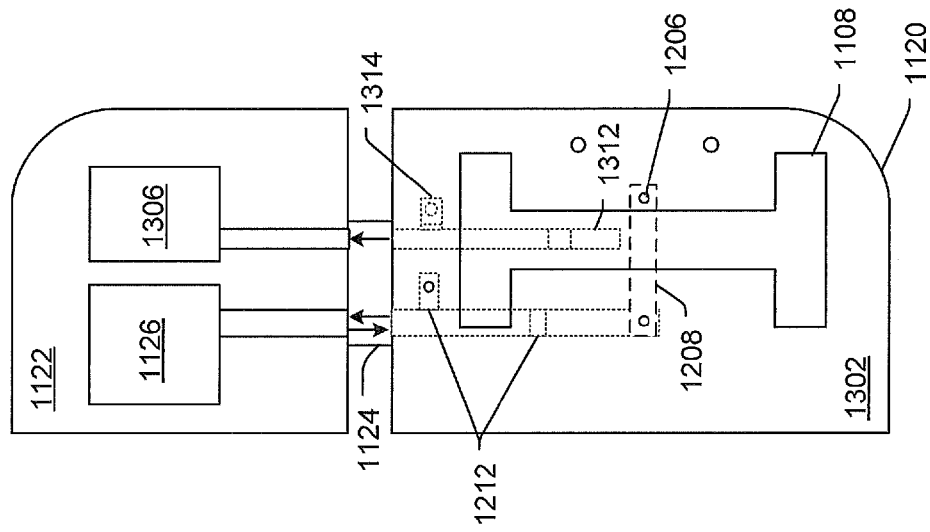
FIGS. 13A-13E are schematic illustrations of antenna systems for use inside an implantable medical device according to various embodiments.
Figure 13B:
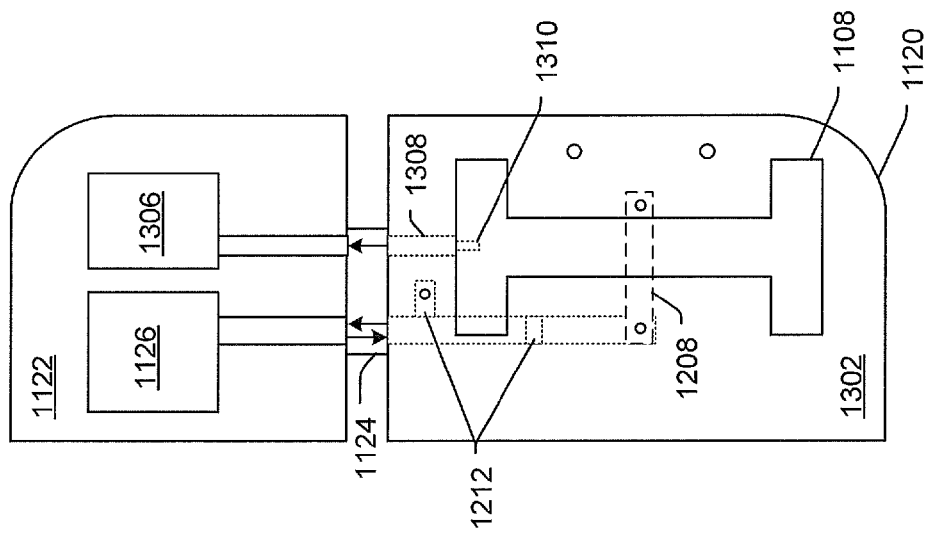
Figure 13A:
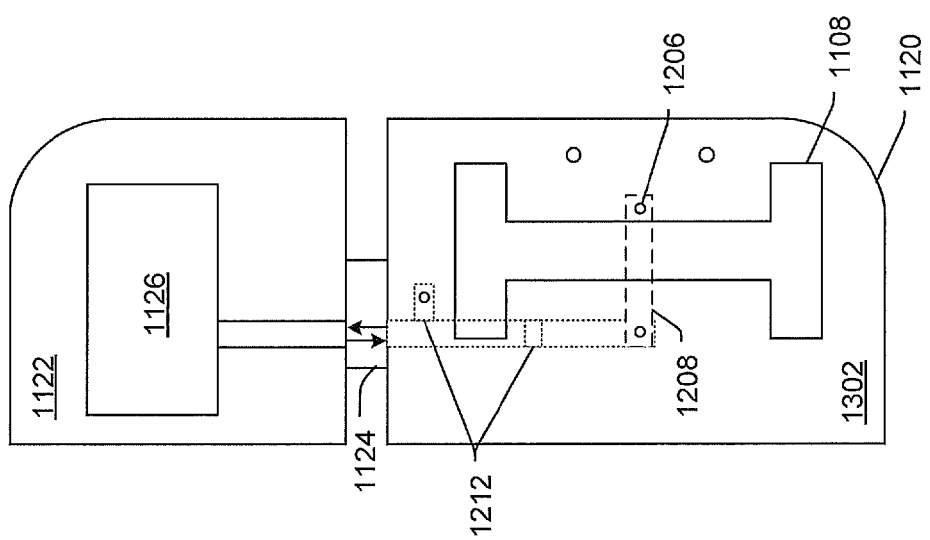

FIG. 13A depicts a top view of a first embodiment of an antenna system. As explained above, the antenna system includes the first circuit board 1120 including the antenna 1108 and the second circuit board 1122 including the communication circuitry 1126. The first circuit board 1120 is coupled to the second circuit board 1122 by the flexible circuit 1124. The antenna 1108 is coupled to the feed line 1208 by the conductive via 1206 and the matching components 1212 are coupled to the feed line 1208.

In FIG. 13B, a second antenna 1310 is added to the antenna system depicted in FIG. 13A. In the view depicted in FIG. 13B, the second antenna 1310 is positioned within the radiating slot of the antenna 1108 (also referred to herein as the "first antenna" to distinguish from the second antenna 1310). In a particular embodiment, the second antenna 1310 may be located on a bottom layer of the first circuit board 1120 and the first antenna 1108 may be located on a top layer of the first circuit board 1120. The second antenna 1310 may be a surface-mountable chip antenna and may be housed in a small form-factor ceramic or polymer package. In another embodiment, the antenna 1108 is positioned on the same side of the circuit board 120 or on another layer of the circuit board 120 relative to the second antenna 1310. In other embodiments, the second antenna 1310 is not positioned behind the opening 1030 of the conductive housing 1002, is not positioned within or behind the radiating slot of the first antenna 1108, or both.

In the embodiment illustrated in FIG. 13B, the first antenna 1108 may be a primary communication antenna and the second antenna 1310 may be a wake-up antenna. For example, the second antenna 1310 may be used to receive a wake-up signal from a device external to a patient in which an IMD is implanted. In response to the wake-up signal, the wake-up circuitry 1306 may cause the communication circuitry 1126 to transition from a sleep state in which the communication circuitry 1126 is inactive to an awake state in which the communication circuitry 1126 is active. The communication circuitry 1126 may then send signals to and receive signals from the device external to the patient or care provider. For example, the communication circuitry 1126 may use the first antenna 1108 to send information regarding sensed conditions within the patient or within the IMD to the device external to the patient. In another example, the communication circuitry 1126 may receive information from the device external to the patient via the first antenna 1108 to program the IMD to perform various therapeutic functions, such as providing stimulation to the tissue of the patient. Alternatively, the first antenna 1108 may be the wake-up antenna and the second antenna 1310 may be the primary communication antenna.

When the antenna system illustrated in FIG. 13B is positioned in the conductive housing 1102 of the IMD 1000 of FIGS. 11 and 12, the wake-up signal may propagate through the opening 1104 and through the radiating slot of the first antenna 1108 to be received by the second antenna 1310. Thus, positioning the second antenna 1310 within the radiating slot of the first antenna 1108 further enables efficient use of space within the IMD 1000. The second antenna 1310 may be a surface mountable component, such as a ceramic antenna, or it may be a planar antenna.

The embodiment illustrated in FIG. 13C depicts another configuration of a second antenna 1312. In the embodiment illustrated in FIG. 13C, the second antenna 1312 may include a conductive element (e.g., a metal layer) formed on or coupled to a layer of the first circuit board 1120. For example, the second antenna 1312 may be formed on or coupled to the bottom layer of the first circuit board 1120. Second matching components 1314 may be coupled to the second antenna 1312 to improve performance of the second antenna 1312 at a frequency of the wake-up signal. For example, the matching components 1212 may facilitate communications of the first antenna 1108 at a frequency of about 400 MHz and the second matching components 1314 may facilitate communications of the second antenna 1312 at a frequency of about 2.45 GHz.

Figure 13E:
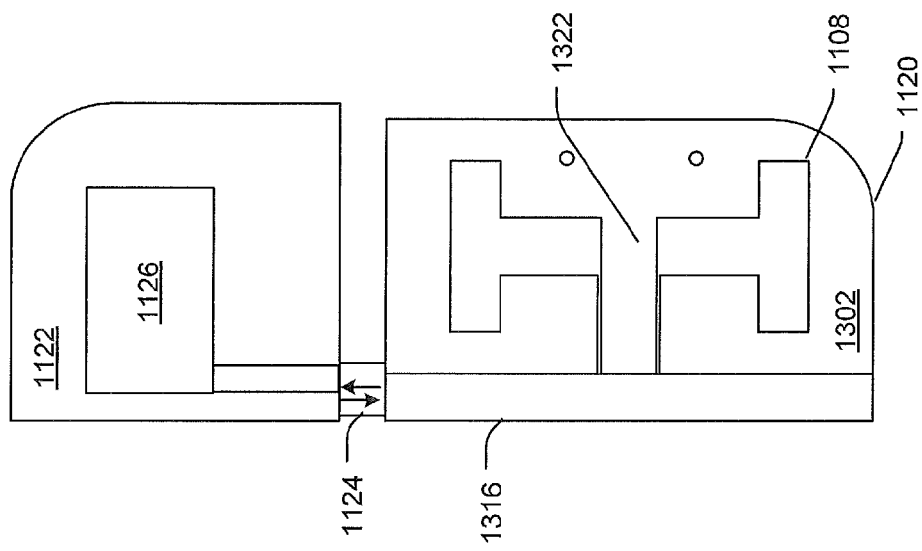
Figure 13D:
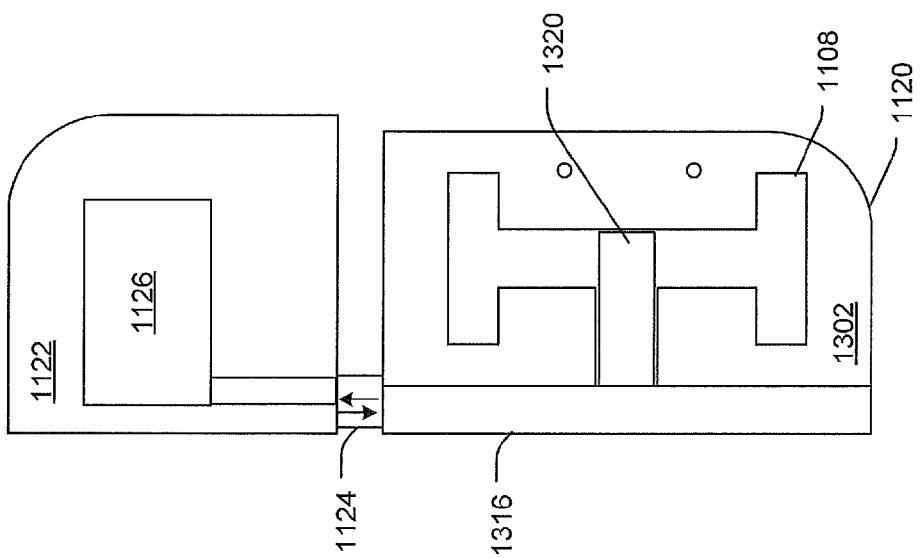

FIGS. 13D and 13E illustrate embodiments in which a feed line of the first antenna is located on the same surface of the first circuit board 1120 as the first antenna 1108. In FIGS. 13D and 13E, the first antenna 1108 includes the conductive layer 1302 on the top surface of the first circuit board 1120 and a communication line 1316 is located on the top surface of the first circuit board 1120. In FIG. 13D, the communication line 1316 couples an open ended feed line 1320, located on the top surface of the first circuit board 1120, to the communication circuitry 1126. In FIG. 13E, the communication line 1316 couples a shorted feed line 1320 located on the top surface of the first circuit board 1120, to the communication circuitry 1126.

The embodiments illustrated in FIGS. 13D and 13E may also be used with a second antenna, such as the second antenna 1310 of FIG. 13B or the second antenna 1312 of FIG. 13C. When the second antenna is present, the second antenna may be located on the same side of the first circuit board 1120 as the first antenna or on an opposite side.

Figure 14:
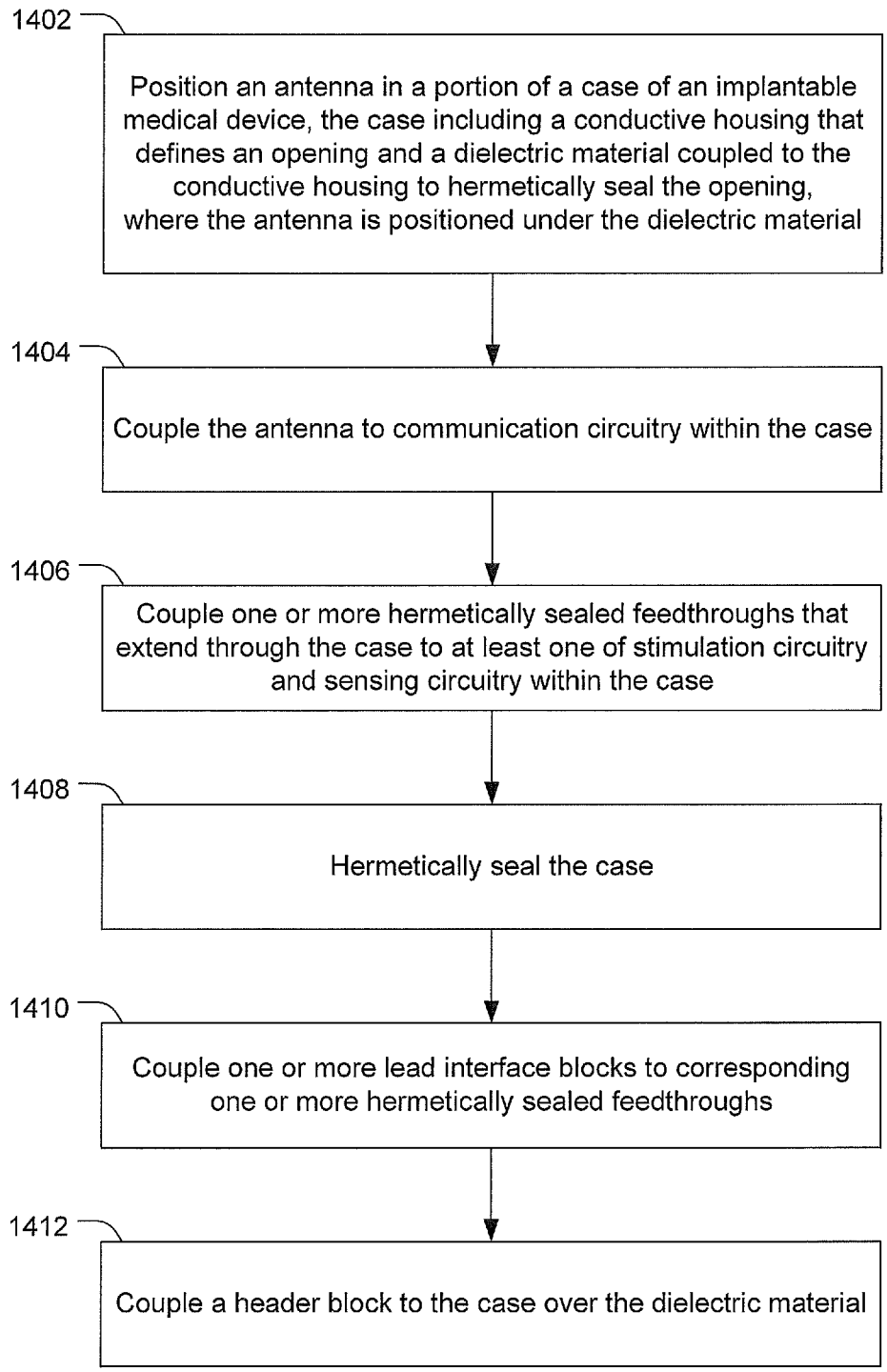
FIG. 14 is a flow chart of a method of manufacturing an implantable medical device according to a particular embodiment.

FIG. 14 is a flow chart of a method of manufacturing an implantable medical device (IMD) according to a particular embodiment. The method may be used to manufacture the IMD 1000 of FIG. 10 or the IMD 1100 of FIGS. 11 and 12. The method may include, at 1402, positioning an antenna in a portion of a case of the IMD. The case may include a conductive housing that defines an opening. A dielectric material may be coupled to the conductive housing to hermetically seal the opening, and an antenna may be positioned under the dielectric material.

The method may also include, at 1404, coupling the antenna to communication circuitry. For example, the antenna may include the first antenna 1012 of FIG. 10, which may be coupled to the communication circuitry 1014. In another example, the antenna may include the second antenna 1032, which may be coupled to the wake-up circuitry 1034. In still another example, the antenna may include one of the antennas 1108, 1310 or 1312 of FIG. 11, 12, or 13A-13E, which may be coupled to the communication circuitry 1126 or the wake-up circuitry 1306 via the flexible circuit 1124.

The method may include, at 1406, coupling one or more hermetically sealed feedthroughs that extend through the case to at least one of stimulation circuitry and sensing circuitry within the case. For example, the one or more hermetically sealed feedthroughs may include the feedthroughs 1044 of FIG. 10. In this example, the feedthroughs 1044 may be coupled to the medical circuitry 1046, which may include sensing circuitry, other circuitry related to gathering data or providing therapy to a patient, or any combination thereof. The feedthroughs may extend through the dielectric material, through the conductive housing, or one or more of the feedthroughs may extend through the dielectric material and one or more of the feedthroughs may extend through the conductive housing.

The method may include, at 1408, hermetically sealing the case. For example, the conductive housing of the case may include multiple pieces which may be coupled together to form a hermetic seal. The pieces of the conductive housing may be welded, brazed, soldered, adhered or otherwise sealed together.

The method may include, at 1410, coupling one or more lead interface blocks to corresponding one or more hermetically sealed feedthroughs. For example, the lead interface blocks may include the lead interface blocks 1040 of FIG. 10 which are coupled through the feedthroughs 1044 to the medical circuitry 1046 within the conductive housing 1002. In another example, the lead interface blocks may include the lead interface blocks 1132 of FIG. 11, which may be coupled to circuitry 1130 within the conductive housing 1102 via one or more hermetically sealed feedthroughs (not shown). The lead interface blocks may be coupled to the corresponding hermetically sealed feedthroughs before the case is sealed or after the case is sealed.

The method may include, at 1412, coupling a header block to the case over the dielectric material. For example, the header block may include the header block 1202 of FIG. 12. In a particular embodiment, the header block may be coupled to the case at the same time the lead interface blocks are coupled to the feedthroughs. For example, lead interface blocks may be embedded within or integral with the header block such that positioning the header block also positions the lead interface blocks.

Figure 15:
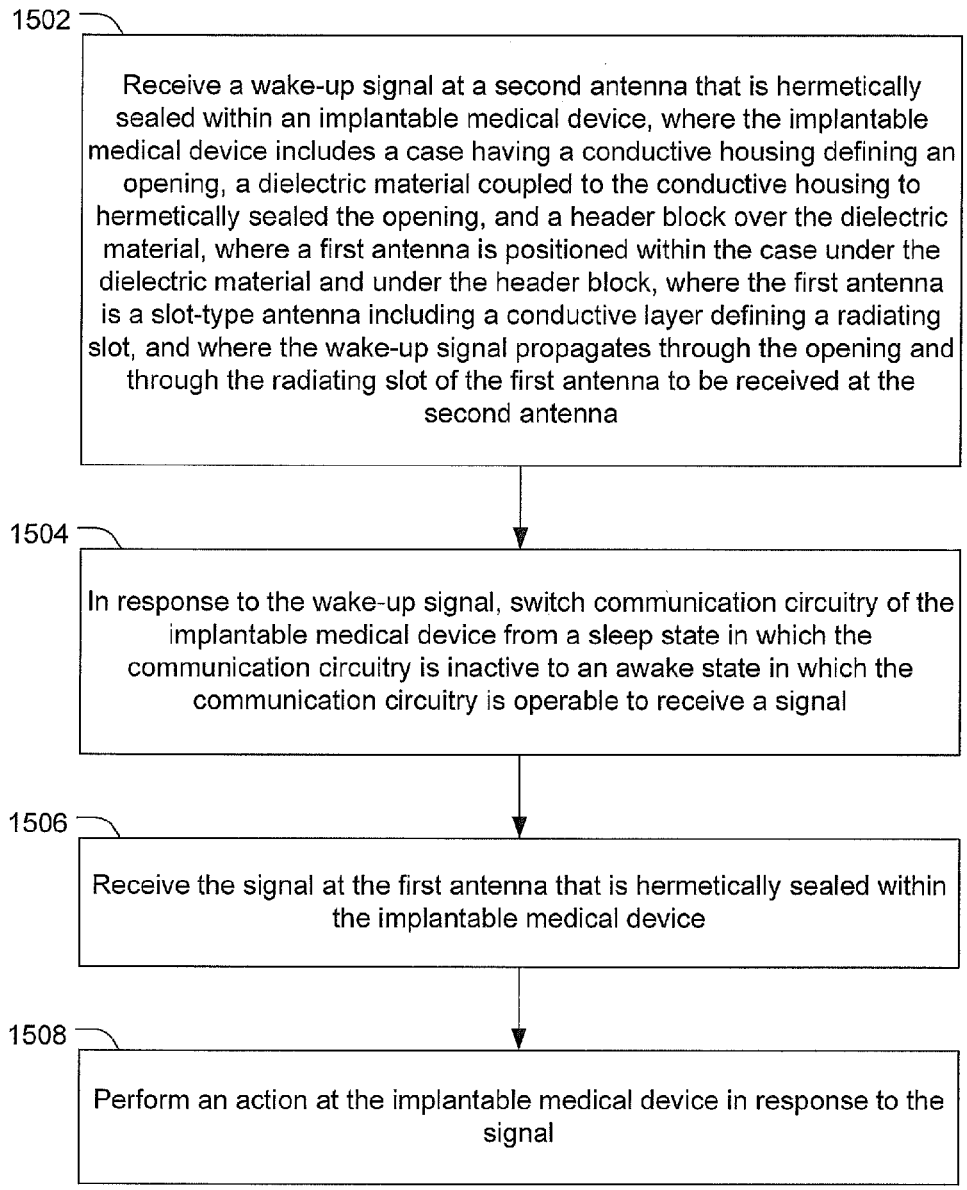
FIG. 15 is a flow chart of a method of communicating with an implantable medical device according to a particular embodiment.

FIG. 15 is a flow chart of a method of communicating with an implantable medical device (IMD) according to a particular embodiment. The method may be performed by the IMD 1000 of FIG. 10 or the IMD 1100 of FIGS. 11 and 12. The method may include, at 1502, receiving a wake-up signal at a second antenna that is hermetically sealed within the IMD. For example, the IMD may be the IMD 1000 of FIG. 10 or the IMD 1100 of FIGS. 11 and 12, and the second antenna may correspond to the second antenna 1032 of FIG. 10, the wake-up antenna 1310 of FIG. 13B or the wake-up antenna 1312 of FIG. 13C. The IMD may include a case having a conductive housing that defines an opening. A dielectric material may be coupled to the conductive housing to hermetically seal the opening and a header block may be located over the dielectric material. A first antenna and the second antenna may be positioned within the case under the dielectric material and under the header block. In a particular embodiment, the first antenna is a planar antenna, such as a slot-type antenna or another planar antenna. To illustrate, the first antenna may include a conductive layer defining a radiating slot. In this example, the second antenna may be positioned within or beneath the radiating slot. Thus, the wake-up signal may propagate through the opening of the conductive housing and through the radiating slot of the first antenna to be received at the second antenna.

In response to the wake-up signal, communication circuitry of the IMD may be switched from a sleep state in which the communication circuitry is inactive to an awake state in which the communication circuitry is operable to receive signals, at 1504. In a particular embodiment, the communication circuitry may transition to the awake state in response to a signal received at the first antenna or in response to another event, such as passage of a particular period of time. In this embodiment, the IMD may not include the second antenna. For example, only the first antenna may be positioned within the case under the dielectric material and under the header block.

The method may include, at 1506, receiving a signal at the first antenna, which is hermetically sealed within the IMD. The IMD may perform an action in response to the signal, at 1508. For example, the IMD may deliver electrical stimulation to neural tissue of a patient. In another example, the IMD may sense a condition of the patient (e.g., a heart rate) or of the IMD (e.g., a battery charge level).

Although the description above contains many specificities, these specificities are utilized to illustrate some of the exemplary embodiments of this disclosure and should not be construed as limiting the scope of the disclosure. The scope of this disclosure should be determined by the claims, their legal equivalents and the fact that it fully encompasses other embodiments which may become apparent to those skilled in the art. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods and programs of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising machine-readable media for carrying or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing description of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. An implantable medical device comprising:
a case including a conductive housing defining an opening;
a dielectric material coupled to the conductive housing to hermetically seal the opening;
an antenna within the case under the dielectric material; and
a header block coupled to the case over the dielectric material, wherein the header block directly overlies and completely covers the dielectric material.

2. The implantable medical device of claim 1, wherein the header block comprises a polymer material, the dielectric material comprises a ceramic material, and the conductive housing comprises a metal or metal alloy material.

3. The implantable medical device of claim 1, wherein the header block is formed of a first material that has a first mechanical failure mechanism when implanted within a patient and the dielectric material is formed of a second material that has a second mechanical failure mechanism when implanted within the patient.

4. The implantable medical device of claim 3, wherein the second material is more brittle at body temperature than the first material.

5. The implantable medical device of claim 1, wherein the header block is configured to retain pieces of the dielectric material in event of a catastrophic failure of the dielectric material.

6. The implantable medical device of claim 1, further comprising an insulating layer between the antenna and an interior of the conductive housing.

7. The implantable medical device of claim 1, wherein the antenna is a planar antenna comprising one or more conductive elements disposed on a circuit board within the case.

8. The implantable medical device of claim 1, further comprising communication circuitry within the case and coupled to the antenna, the communication circuitry operable to at least one of:
send a first signal to a device external to the case; or
receive a second signal from the device external to the case.

9. The implantable medical device of claim 8, wherein the antenna is a slot-type antenna including a conductive layer on a surface of a circuit board, the conductive layer defining a radiating slot.

10. The implantable medical device of claim 9, further comprising a second antenna, wherein the second antenna is arranged to receive a second signal that propagates through the opening and through the radiating slot of the antenna.

11. The implantable medical device of claim 10, wherein the conductive layer of the antenna is coupled to a first side of the circuit board and the second antenna is coupled to a second side of the circuit board, the second side opposite the first side.

12. The implantable medical device of claim 10, further comprising wake-up circuitry within the case and coupled to the second antenna, wherein the wake-up circuitry is operable, in response to the second signal received at the second antenna, to cause the communication circuitry to transition from a sleep state in which the communication circuitry is inactive to an awake state in which the communication circuitry is active.

13. The implantable medical device of claim 1, further comprising medical circuitry within the case, the medical circuitry including at least one of therapeutic circuitry or sensing circuitry, wherein the header block includes one or more lead interface blocks connected to the medical circuitry and wherein the one or more lead interface blocks at least partially obscure the antenna.

14. The implantable medical device of claim 1, wherein the case has a first side and a second side opposite the first side, wherein the first side has a recessed portion and a non-recessed portion, wherein a first distance between the second side and the recessed portion of the first side is smaller than a second distance between the second side and the non-recessed portion of the first side, and wherein the antenna is positioned between the second side and the recessed portion of the first side.

15. The implantable medical device of claim 14, wherein the header block extends from the recessed portion of the first side to approximately flush with the non-recessed portion of the first side.

16. A method comprising:
positioning an antenna in a portion of a case of an implantable medical device, the case including:
a conductive housing that defines an opening; and
a dielectric material coupled to the conductive housing to hermetically seal the opening, wherein the antenna is positioned under the dielectric material;
hermetically sealing the case; and
coupling a header block to the case over the dielectric material, wherein the header block directly overlies and completely covers the dielectric material.

17. The method of claim 16, further comprising coupling the antenna to communication circuitry within the case before hermetically sealing the case.

18. The method of claim 16, wherein the header block includes one or more lead interface blocks and the method further comprises:
coupling the one or more lead interface blocks to corresponding one or more hermetically sealed feedthroughs that extend through the case; and
coupling the one or more hermetically sealed feedthroughs to at least one of stimulation circuitry or sensing circuitry within the case.

19. The implantable medical device of claim 1, wherein the header block is configured to protect the dielectric material against catastrophic failure by absorbing impact energy.

20. A method comprising:
receiving a signal at a first antenna that is hermetically sealed within an implantable medical device, wherein the implantable medical device comprises:
a case including a conductive housing defining an opening and a dielectric material coupled to the conductive housing to hermetically seal the opening; and
a header block over the dielectric material, wherein the header block directly overlies and completely covers the dielectric material, wherein the first antenna is positioned within the case under the dielectric material and under the header block; and
performing an action at the implantable medical device in response to the signal.

21. The method of claim 20, further comprising, before receiving the signal:
receiving a wake-up signal at a second antenna that is hermetically sealed within the implantable medical device, wherein the first antenna is a slot-type antenna including a conductive layer defining a radiating slot, and wherein the wake-up signal propagates through the opening and through the radiating slot of the first antenna to be received at the second antenna; and in response to the wake-up signal, switching communication circuitry of the implantable medical device from a sleep state in which the communication circuitry is inactive to an awake state in which the communication circuitry is operable to receive the signal.

22. An implantable medical device comprising:

a case including a conductive housing defining an opening;

a dielectric material coupled to the conductive housing to hermetically seal the opening, wherein the dielectric material is located within an interior of the implantable medical device;

an antenna within the case and located on a first side of the opening; and a header block coupled to the case and located on a second side of the opening that is opposite the first side, wherein the header block completely covers the dielectric material.

* * * * *